United States Patent [19]

Rudy

[11] Patent Number: 5,466,680
[45] Date of Patent: Nov. 14, 1995

[54] METHOD AND COMPOSITIONS FOR ENHANCING WHITE BLOOD CELL FUNCTIONING ON A MUCOSAL OR CUTANEOUS SURFACE

[75] Inventor: Michael A. Rudy, Rochester, N.Y.

[73] Assignee: Cytologics, Inc., Rochester, N.Y.

[21] Appl. No.: 858,290

[22] Filed: Mar. 26, 1992

[51] Int. Cl.⁶ .................. A61K 31/70; A61K 31/195; A61K 38/00

[52] U.S. Cl. .................. 514/57; 514/781; 514/866; 514/885; 514/887; 514/917; 514/921; 514/925; 514/926; 514/927; 514/928; 514/931; 514/932; 514/933; 514/934

[58] Field of Search .................. 514/57, 781, 885, 514/887, 866, 917, 921, 928, 925, 926, 927, 931, 932, 933, 934

[56] References Cited

U.S. PATENT DOCUMENTS

| | | | |
|---|---|---|---|
| 2,556,567 | 6/1951 | Wright et al. | 514/827 |
| 3,337,404 | 8/1967 | Polli et al. | 426/810 |
| 3,703,438 | 11/1972 | Dovgalev et al. | 514/833 |
| 3,809,747 | 5/1974 | Toscano | 424/70 |
| 3,830,910 | 8/1974 | Homsy | 514/833 |
| 3,864,475 | 2/1975 | Willard | 514/785 |
| 3,897,550 | 7/1975 | Reynolds | 514/833 |
| 3,899,579 | 8/1975 | Anderson | 424/601 |
| 3,911,114 | 10/1975 | Cardon | 424/601 |
| 3,935,067 | 1/1976 | Thayer | 435/252.1 |
| 3,993,750 | 11/1976 | Fox | 424/601 |
| 3,993,751 | 11/1976 | Zinke | 424/601 |
| 4,024,237 | 5/1977 | Eichel et al. | 424/49 |
| 4,048,123 | 9/1977 | Hramchenko et al. | 514/846 |
| 4,070,452 | 1/1978 | Borchorst | 424/70 |
| 4,077,842 | 3/1978 | Cory | 435/233 |
| 4,084,747 | 4/1978 | Alliger | 514/816 |
| 4,229,430 | 10/1980 | Fahim et al. | 424/49 |
| 4,238,482 | 12/1980 | Peyman et al. | 536/112 |
| 4,276,287 | 6/1981 | Cabardo et al. | 424/49 |
| 4,315,001 | 2/1982 | Blough | 536/1.1 |
| 4,363,794 | 12/1982 | Ochiai et al. | 424/52 |
| 4,404,192 | 9/1983 | Suzuki | 514/23 |
| 4,443,432 | 4/1984 | Garabedian et al. | 514/912 |
| 4,447,562 | 5/1984 | Ivani | 523/106 |
| 4,465,673 | 8/1984 | Tanaka et al. | 536/18.1 |
| 4,468,381 | 8/1984 | Mitra et al. | 514/937 |
| 4,472,376 | 9/1984 | Kamishita | 424/DIG. 15 |
| 4,478,853 | 10/1984 | Chaussee | 424/65 |
| 4,489,535 | 12/1984 | Veltman | 252/1 |
| 4,499,076 | 2/1985 | Ohashi et al. | 514/58 |
| 4,503,037 | 3/1985 | Szijjarto et al. | 514/928 |
| 4,550,022 | 10/1985 | Garabedian et al. | 514/816 |
| 4,552,814 | 6/1985 | Nonomura et al. | 514/54 |
| 4,582,705 | 4/1986 | Primes et al. | 514/474 |
| 4,600,711 | 7/1986 | Swerczek | 514/23 |
| 4,603,122 | 7/1986 | Blough | 514/23 |
| 4,609,640 | 9/1986 | Morishita et al. | 514/12 |
| 4,610,874 | 9/1986 | Matravers | 514/801 |
| 4,620,979 | 11/1986 | Schachar | 514/912 |
| 4,634,591 | 1/1987 | Westerman | 424/48 |
| 4,640,911 | 2/1987 | Baschang et al. | 514/42 |
| 4,645,662 | 2/1987 | Nakashima et al. | 424/48 |
| 4,664,915 | 5/1987 | Simonian | 514/164 |
| 4,670,256 | 6/1987 | Doran | 424/93 |
| 4,696,917 | 9/1987 | Lindstrom et al. | 514/54 |
| 4,711,780 | 12/1987 | Fahim | 514/562 |
| 4,711,879 | 12/1987 | Baschang et al. | 514/42 |
| 4,713,241 | 12/1987 | Wakisaka et al. | 435/252.5 |
| 4,717,713 | 1/1988 | Zatz et al. | 514/57 |
| 4,725,433 | 2/1988 | Matravers | 514/938 |
| 4,725,586 | 2/1988 | Lindstrom et al. | 514/54 |
| 4,755,378 | 7/1988 | Buxton et al. | 514/966 |
| 4,761,402 | 8/1988 | Williams et al. | 514/54 |
| 4,762,825 | 8/1988 | Takeo et al. | 514/54 |
| 4,772,591 | 9/1988 | Meisner | 514/23 |
| 4,788,060 | 11/1988 | Endicott et al. | 424/443 |
| 4,811,747 | 3/1989 | Reis | 424/70 |
| 4,877,620 | 10/1989 | Loew et al. | 424/451 |
| 4,877,773 | 10/1989 | Turner | 514/23 |
| 4,880,783 | 11/1989 | Mentzer et al. | 536/26 |
| 4,886,665 | 12/1989 | Kovacs | 424/195.1 |
| 4,886,786 | 12/1989 | Lindstrom et al. | 514/54 |
| 4,900,722 | 2/1990 | Williams et al. | 514/54 |
| 4,900,730 | 2/1990 | Miyauchi | 514/12 |
| 4,906,460 | 3/1990 | Kim et al. | 514/773 |
| 4,906,461 | 3/1990 | Chambers | 424/195.1 |
| 4,952,392 | 8/1990 | Thame | 424/57 |
| 4,970,220 | 11/1990 | Chaussee | 514/844 |
| 5,026,547 | 6/1991 | Imamura et al. | 424/122 |
| 5,073,377 | 12/1991 | Alexander et al. | 424/458 |

FOREIGN PATENT DOCUMENTS

| | | |
|---|---|---|
| 0382551A2 | 8/1990 | European Pat. Off. . |
| 2112285 | 7/1983 | United Kingdom . |
| WO90/07007 | 6/1990 | WIPO . |

OTHER PUBLICATIONS

Podzorski et al., 1990, "Different effects of native Candida albicans mannan and mannan-derived oligosaccharides on the antigen-stimulated lymphoproliferation in vitro," J. Immunol., 144(2):707–716.

Kaneko et al., 1989, "Activity of lentinan against cancer and AIDS," Int. J. Immunotherapy 5(4):203–213.

Mangeney et al., 1989, "Direct activation of human B lymphocytes by Candida albicans-derived mannan antigen," Cell. Immunol., 122:329–337.

McDermott et al., 1988, "Ophthalmic irrigants: A current review and update," Ophthalmic Surgery 19(10):724–733.

(List continued on next page.)

Primary Examiner—Ronald W. Griffin
Attorney, Agent, or Firm—Pennie & Edmonds

[57] ABSTRACT

The present invention relates to a method for enhancing white blood cell functioning and metabolism on a mucosal surface of a mammal. The present invention also relates to a method for treating or preventing a condition in a mammal caused by the presence of a disease-causing agent on a mucosal surface or a cutaneous surface wherein the disease-causing agent can be diminished by the actions of the white blood cells. The present invention yet also relates to a method for healing a wound of a mucosal or cutaneous surface. The present invention also relates to compositions for use in such methods.

98 Claims, No Drawings

OTHER PUBLICATIONS

Gil–Fernandez et al., 1987, "Antiviral activity of uridine 5'–diphosphate glucose analogues against some enveloped viruses in cell culture," Antiviral Research 8:299–310.

Rosenfeld et al., 1986, "Comparison of intraocular irrigating solutions in pars plana vitrectomy," Ophthalmol., 93(1):109–115.

Glasser et al., 1985, "Effects of intraocular irrigating solutions on the corneal endothelium after in vivo anterior chamber irrigation," Am. J. Ophthalmol., 99:321–328.

Kern et al., 1982, "Failure of 2–deoxy–D–glucose in the treatment of experimental cutaneous and genital infections due to herpes simplex virus," J. Infectious Diseases 146(2):159–166.

Spivack et al., 1982, "A study of the antiviral mechanism of action of 2–deoxy–D–glucose: Normally glycosylated proteins are not strictly required for herpes simplex virus attachment but increase viral penetration and infection," Virology 123:123–138.

Burke et al., 1981, "Safety evaluation of BBS plus in pediatric intraocular surgery," J. Pediatric Ophthalmology and Strabismus 18(3):45–49.

Blough and Giuntoli, 1979, "Successful treatment of human genital herpes infections with 2–deoxy–D–glucose," JAMA 241(26):2798–2801.

Edelhauser et al., 1978, "Intraocular irrigating solutions," Arch. Ophthalmol., 96:526–510.

Knowles and Person, 1976, "Effects of 2–deoxyglucose, glucosamine, and mannose on cell fusion and the glycoproteins of herpes simplex virus," J. Virol., 18(2):644–651.

METHOD AND COMPOSITIONS FOR ENHANCING WHITE BLOOD CELL FUNCTIONING ON A MUCOSAL OR CUTANEOUS SURFACE

TECHNICAL FIELD

The present invention relates to a method for enhancing white blood cell functioning and metabolism on a mucosal surface of a mammal. The present invention also relates to a method for treating or preventing a condition in a mammal caused by the presence of a disease-causing agent on a mucosal surface or a cutaneous surface wherein the disease-causing agent can be diminished by the actions of the white blood cells. The present invention yet also relates to a method for healing a wound of a mucosal or cutaneous surface. The present invention also relates to compositions for use in such methods.

BACKGROUND OF THE INVENTION

Mammals have systems that provide to cells an energy source, chemical nutrients, a proper extracellular pH, a natural osmotic environment (osmolality), a favorable fluid environment with respect to viscosity and a balanced ionic environment. This is accomplished through the production and circulation of fluids and, thereby, permits the cells to perform their intended function.

The primary fluid in mammals is blood. Blood carries nutrients and essential chemicals, oxygen and carbon dioxide, helps to regulate body temperature and pH, carries cellular waste products away from the cells and transports water to and from cells.

In addition to blood, other fluids participate in maintaining the physical and chemical environment of individual cells. These fluids include lymph, intestinal fluid, cerebrospinal fluid and mucus.

Epithelial membranes cover virtually the entire body surface of mammals. Epithelial membranes onto which mucus is secreted are called mucosal surfaces. Mucus is a clear, viscid secretion containing water, inorganic salts, the protein mucin and other components. Epithelial membranes that are not mucosal surfaces are cutaneous surfaces.

The epithelial membranes consist of epithelial cells. Also, white blood cells (leukocytes), which have left the blood, are present on or near mucosal surfaces and epithelial membranes. The white blood cells include neutrophils, macrophages, lymphocytes, lymphocyte derived cells such as natural killer cells, and eosinophils and basophils. In addition, in the case of wounds, cells that are not blood cells, called fibroblasts, move into the area of the epithelial membrane that has been wounded.

The white blood cells, which are the cellular components of the immune system, are involved in maintaining a healthy state on mucosal surfaces and combatting those disease-causing agents that can be diminished by the actions of white blood cells on such surfaces. In addition, white blood cells, epithelial cells and fibroblasts play a role in wound-healing on mucosal surfaces and cutaneous surfaces.

In a healthy state, these epithelial cells, white blood cells and fibroblasts function properly and are supplied with an energy source, chemical nutrients, and the mucosal surface maintains a proper pH, a natural osmolality and a favorable fluid environment with respect to viscosity and a balanced ionic environment. In a healthy state, those disease-causing agents that can be diminished by the actions of white blood cells may be present on a mucosal surface, but the white blood cells are able to prevent such disease-causing agents from multiplying in sufficient numbers and, thereby, result in an overt disease. However, if one or more of these factors is out of balance and the white blood cells are inhibited from performing their function, then, for example, an overgrowth of Candida organisms on the vaginal mucosal surface can occur, thereby producing an overt infection. In addition, the infecting organisms consume energy and chemical nutrients intended for the white blood cells and, thereby, alter the pH, osmolality, fluid environment and ionic environment, which can exacerbate the infection by further inhibiting white blood cells functioning. These factors are also out of balance when a wound occurs and, therefore, the white blood cells, epithelial cells and fibroblasts are inhibited and cannot heal the wound as readily as if these cells could function at their optimal level.

Accordingly, there is a need for compositions and methods for treating or preventing a condition in a mammal caused by the presence of a disease-causing agent on a mucosal surface or a cutaneous surface wherein the disease-causing agent can be diminished by the actions of the white blood cells. Also, there is a need for compositions and methods for healing a wound of a mucosal surface or cutaneous surface.

SUMMARY OF THE INVENTION

The present invention relates to a method for treating or preventing a condition in a mammal caused by the presence of a disease-causing agent on a mucosal surface or a cutaneous surface wherein said disease-causing agent can be diminished by the actions of the white blood cells of a mammal comprising contacting the mucosal or the cutaneous surface of a mammal in need of said treatment or prevention with an effective amount to treat or prevent said condition of a composition comprising:

(a) an energy source for white blood cells;

(b) a source of cations to provide a cation selected from the group consisting of sodium, potassium, magnesium, calcium and mixtures thereof;

(c) a source of anions to provide an anion selected from the group consisting of chloride, sulfate, phosphate, bicarbonate and mixtures thereof;

wherein the pH of said composition is from about 4 to about 10 and the osmolality of said composition is from about 140 mOsm/kg to about 2,000 mOsm/kg; with the proviso that said mucosal surface is not the oral cavity. Such composition can also be utilized for enhancing white blood cell functioning and metabolism on a mucosal surface of a mammal.

The present invention also relates to a method for healing a wound of a mucosal or cutaneous surface of a mammal comprising contacting the mucosal surface or the cutaneous surface of a mammal in need of said healing with a therapeutically effective amount of a composition comprising:

(a) an energy source for white blood cells;

(b) a source of cations to provide a cation selected from the group consisting of sodium, potassium, magnesium, calcium and mixtures thereof;

(c) a source of anions to provide an anion selected from the group consisting of chloride, sulfate, phosphate, bicarbonate and mixtures thereof;

wherein the pH of said composition is from about 4 to about 10 and the osmolality of said composition is from about 140 mOsm/kg to about 2,000 mOsm/kg.

The present invention also provides compositions useful in such methods.

DETAILED DESCRIPTION OF THE INVENTION

The present invention relates to a method for treating or preventing a condition in a mammal caused by the presence of a disease-causing agent on a mucosal surface or a cutaneous surface wherein said disease-causing agent can be diminished by the actions of the white blood cells of a mammal comprising contacting the mucosal or the cutaneous surface of a mammal in need of said treatment or prevention with an effective amount to treat or prevent said condition of a composition comprising:

(a) an energy source for white blood cells;

(b) a source of cations to provide a cation selected from the group consisting of sodium, potassium, magnesium, calcium and mixtures thereof;

(c) a source of anions to provide an anion selected from the group consisting of chloride, sulfate, phosphate, bicarbonate and mixtures thereof;

wherein the pH of said composition is from about 4 to about 10 and the osmolality of said composition is from about 140 mOsm/kg to about 2,000 mOsm/kg.; with the proviso that said mucosal surface is not the oral cavity. Such composition can also be utilized for enhancing white blood cell functioning and metabolism on a mucosal surface of a mammal.

The present invention also relates to a method for healing a wound of a mucosal surface or cutaneous surface of a mammal comprising contacting the mucosal surface or the cutaneous surface of a mammal in need of said healing with a therapeutically effective amount of a composition comprising:

(a) an energy source for white blood cells;

(b) a source of cations to provide a cation selected from the group consisting of sodium, potassium, magnesium, calcium and mixtures thereof;

(c) a source of anions to provide an anion selected from the group consisting of chloride, sulfate, phosphate, bicarbonate and mixtures thereof;

wherein the pH of said composition is from about 4 to about 10 and the osmolality of said composition is from about 140 mOsm/kg to about 2,000 mOsm/kg.

Without being bound by theory, the present invention is predicated on the enhancement of white blood cell functioning and metabolism on a mucosal surface of a mammal. In a healthy state, the white blood cells on a mucosal surface function properly and are supplied with an energy source, chemical nutrients and the mucosal surface maintains a proper pH, a natural osmolality, a favorable fluid environment with respect to viscosity and a balanced ionic environment. Thus, in a healthy state, disease-causing agents that can be diminished by the actions of white blood cells may be present on a mucosal surface, but the white blood cells are able to prevent such disease-causing agents from multiplying in sufficient numbers and, thereby, result in overt disease. However, if one or more of these factors is out of balance, e.g., the white blood cells are not supplied with a sufficient energy source, then the white blood cells would be inhibited from performing their function, thereby permitting such a disease-causing agent to multiply to produce an overt disease. This lack of balance can be caused by, for example, excessive sugar in the diet, antibiotics, humid weather, birth control pills, stress, or by something that decreases the efficacy of the white blood cells, for example, diabetes, radiation, chemotherapy or AIDS. Thus, the present invention provides compositions that can be utilized to provide an optimum environment on a mucosal surface, thereby permitting the white blood cells to function optimally and, thereby, treat or prevent such disease-causing agents that are present on the mucosal surface from producing an overt disease.

The present invention can also be utilized to treat or prevent a condition in a mammal caused by the presence of a disease-causing agent on a cutaneous surface wherein the disease-causing agent can be diminished by the action of white blood cells, e.g., the treatment of a skin lesion resulting from herpes simplex virus infection, primary or recurrent.

Also, without being bound by theory, the present invention is predicated on the enhancement of white blood cell, epithelial cell and fibroblast functioning and metabolism for healing a wound of a mucosal surface or cutaneous surface. It is believed that the compositions of the present invention provide such enhancement of white blood cells, epithelial cells and fibroblasts, which results in faster wound healing.

Accordingly, the compositions of the present invention can be utilized to treat or prevent any condition caused by a disease-causing agent on a mucosal surface or cutaneous surface of a mammal that can be diminished by the actions of white blood cells. The compositions of the present invention can also be utilized for healing a wound of a mucosal or cutaneous surface. The compositions can be utilized to heal a wound or treat or prevent such conditions on a cutaneous surface or on any mucosal surface of a mammal, which mucosal surface also includes the transition areas between skin and mucous membranes, e.g., the lips, the major and minor labia, the ano-rectal junction and the outer portion of the nasal epithelium. Nonlimiting examples of the cutaneous surfaces to which the compositions of the present invention can be applied include the skin and vulva. Nonlimiting examples of the mucosal surfaces to which the compositions of the present invention can be applied include the conjunctiva, the mucosa of the inner surface of the eye lid, the nasal mucosa, the paranasal sinus mucosa, gingivae, the vaginal mucosa, the cervical mucosa, the ano-rectal mucosa, urinary bladder mucosa, urethral mucosa and tracheal and bronchial mucosae.

Nonlimiting examples of conditions of disease-causing agents on a mucosal surface or cutaneous surface that can be diminished by the actions of white blood cells include infections—including bacterial, fungal, viral, protozoal and chlamydial infections—and inflammatory diseases. Nonlimiting examples of such infections include conjunctivitis, nasal sinus infection, oral Candidiasis, Candida vulvovaginitis, Enterococcus vulvovaginitis, *E. coli*, vulvovaginitis, chlamydial vulvovaginitis, Trichomonas vaginitis, genital human pappillomavirus—including condylomata acuminata epithelial and subepithelial lesions caused by herpes simplex virus (Types 1 and 2), herpes zoster virus and varicella zoster virus, cutaneous Candidiasis and warts. Nonlimiting examples of such inflammatory diseases include allergic conjunctivitis, chronic sinusitis, acute and chronic rhinitis and allergic rhinitis, gingivitis, chronic vulvo-vestibulitis and anal pruritis. Other such conditions include dental plaque, dry eye syndrome, oral radiation mucositis, the effects of radiation induced salivary dysfunction, the effects on oral soft tissues resulting from xerostomia, vaginitis and vaginal irritation secondary to pelvic radiation therapy, systemic cancer chemotherapy and antidepressant medications.

Nonlimiting examples of wounds of a mucosal surface or cutaneous surface of a mammal include burns, ophthalmic surgical wounds, wounds associated with corneal grafting, nasal surgical wounds, oral surgical wounds, radiation cystitis, radiation vaginitis, vaginal surgical wounds, and surgical wounds, radiation proctitis, wounds of bleeding hemorrhoids, plastic surgery wounds, wounds associated with skin grafting, thermal burns, chemical burns, radiation burns, general surgical wounds and non-surgical traumatic wounds, e.g., lacerations and abrasions.

A. The Energy Source

The energy source can be any molecule that can be transported through the cell membranes of white blood cells and utilized in metabolic pathways of white blood cells to produce usable chemical energy for such cells. The energy sources all feed into or are part of some common metabolic pathways that result in the generation of usable energy in the form of chemical bond formation, generally a phosphate bond in the compound adenosine triphosphate (ATP). Nonlimiting examples of energy sources include metabolic intermediates involved in energy production, such as citric acid, acetic acid, pyruvic acid, lactic acid and pharmaceutically acceptable salts thereof; glucose-6-phosphate, and fructose-6-phosphate; monosaccharides such as D-mannose, D-galactose, D-fructose and D-glucose (dextrose); oligosaccharides such as maltose, lactose and sucrose; polysaccharides such as glycogen, starch (amylose and amylopectin); metabolizable lipids such as fatty acids and neutral fats; amino acids; oligopeptides and metabolizable proteins, for example, actin and myosin, and mixtures thereof. Preferred energy sources are the monosaccharides, with D-glucose being most preferred.

D-glucose is an energy source basic to the metabolism of all the cell types that the compositions are intended to benefit.

The biochemical pathways involved in energy production are known to those skilled in the biochemical arts. All the energy sources that can be used in the compositions of the present invention are metabolized along these known pathways, and all produce a known amount of energy (theoretical) per amount metabolized.

When an energy source (amino acid, metabolizable protein, sugar other than D-glucose, carbohydrate, fat, fatty acid, metabolic intermediate, etc.) that is not D-glucose is used in a composition, the amount to be used can be calculated by calculating the amount based on "energy equivalence" with D-glucose. The amount of energy that D-glucose would produce, if used in the composition, is calculated, and an amount of the non-D-glucose energy source is used that would produce the same amount of energy when metabolized as the D-glucose would produce.

In addition, these energy sources for white blood cells are also energy sources for epithelial cells and fibroblasts and, therefore, the compositions of the present invention are particularly useful for healing a wound of a mucosal or cutaneous surface.

It is preferred that the energy source be present in an amount of energy equivalence to D-glucose of from about 0.10 to about 10 weight percent D-glucose of the composition and more preferably from about 0.40 to about 2.5 weight percent D-glucose of the composition.

B. Source of Cations And Anions

The fluids within living cells of mammals and extracellular fluids of mammals naturally contain many chemical substances in ionic form. There are mechanisms present in the cells of mammals that act to control and maintain the ionic content of the intracellular fluid. The ionic composition of extracellular fluid differs significantly from the ionic composition of intracellular fluid. For example, in intracellular fluid, the concentration of potassium is much higher and the concentration of sodium and calcium are much lower than that of extracellular fluid. Also, although cellular mechanisms perform work to maintain the ionic composition and balance of the intracellular fluid, the process of maintaining the intracellular ionic composition is made much more difficult as the ionic composition of extracellular fluid deviates farther and farther from normal.

On mucosal surfaces and cutaneous surfaces to which the compositions of the present invention are applied, the ionic compositions of the extracellular fluids are generally abnormal., made so by, for example, certain disease-causing agents.

The compositions of the present invention are intended to provide an ionic environment for white blood cells, epithelial cells and fibroblasts that reflects or is analogous to the ionic composition of normal extracellular fluid.

The ionic component of the composition of the present invention is a source of cations to provide a cation selected from the group consisting of sodium, potassium, magnesium, calcium and mixtures thereof, with sodium being preferred, and a source of anions to provide an anion selected from the group consisting of chloride, sulfate, phosphate, bicarbonate and mixtures thereof, with chloride being preferred.

Sodium ions, along with chloride and bicarbonate ions, are the primary contributors to the osmolality of the extracellular fluid. Sodium ions are present both within cells and in the extracellular fluids, with the extracellular concentration being greater. This concentration gradient is responsible for driving many biological processes.

In addition, sodium ions are utilized for the maintenance of a high intracellular potassium ion concentration by means of an integral membrane bound sodium-potassium pump. The sodium ions are pumped outwardly against the concentration gradient and potassium ions are pumped inwardly against their concentration gradient. Since the concentration of the sodium ions is higher externally, the sodium ions are constantly diffusing into the cell. This diffusion is a cotransport mechanism for the internalization of organic molecules.

Virtually any source of sodium ions can be utilized, but it is preferred that the source be reasonably soluble in water, chemically compatible with other components of the composition and nontoxic.

Nonlimiting examples of a source of cations to provide the sodium cation are sodium chloride, sodium phosphates, sodium acetate, sodium citrate, sodium bicarbonate and sodium sulfate, with sodium chloride being preferred.

Potassium ions are the principal intracellular positively charged ions and are essential to maintaining intracellular osmolality. As with sodium, the concentration gradient across the cell membrane is responsible for driving many biological processes. Also, potassium participates in protein synthesis and carbohydrate utilization.

Potassium ions also behave as catalysts for a variety of reactions, including those associated with carbohydrate, amino acid, protein and fat metabolism, as well as many transphosphorylating reactions.

Virtually any source of potassium ions can be utilized, but, as with sodium ions, it is preferred that the potassium ion source be reasonably soluble in water, chemically compatible with other components of the composition and nontoxic.

Nonlimiting examples of a source of cations to provide the potassium cation are potassium chloride, potassium phosphates, potassium gluconate, potassium citrate, potassium acetate and potassium bicarbonate, with potassium chloride being preferred.

Magnesium ions are electrolytes, which are necessary in a number of enzyme systems. Transfer of a phosphoryl group is a basic reaction in biochemistry. Enzymes that catalyze the transfer of a phosphoryl group from ATP to an acceptor are called kinases. All kinases require magnesium ions for activity. Kinase activity is essential for proper metabolism and energy transfer to occur in cells. Magnesium ions also have a role in cellular mobility and chemotactic responses, including the functioning of complement and its alternative pathway.

Virtually any source of magnesium ions can be utilized, but it is preferred that the magnesium ion source be reasonably soluble in water, chemically compatible with other components of the composition and nontoxic.

Nonlimiting examples of a source of cations to provide the magnesium cations are magnesium sulfate, magnesium chloride, magnesium citrate, magnesium gluconate, magnesium phosphate and magnesium salicylate, with magnesium sulfate and magnesium chloride being preferred and with magnesium sulfate being most preferred.

Calcium ions play a role in intracellular signalling. Calcium ions are sometimes referred to as a "second messenger" in signaling systems of mammals. Also, normal intracellular calcium ion concentrations are necessary for complement and its alternative pathway to lead to lysis of gram negative bacteria or opsonization of gram positive bacteria. Both complement and its alternative pathway rely upon a series of chemical modifications and interactions, some of which are calcium mediated.

Virtually any source of calcium ions can be utilized, but it is preferred that the calcium ion source be reasonably soluble in water, chemically compatible with other components of the composition and nontoxic.

Nonlimiting examples of a source of cations to provide the calcium cations are calcium chloride, calcium gluconate, calcium gluceptate, calcium levulinate, calcium acetate, calcium citrate, calcium hydroxide, calcium lactate, calcium phosphate and calcium saccharate, with calcium chloride being preferred.

Chloride ions also contribute to the osmolality of the extracellular fluid. The extracellular concentration of chloride ion is much higher than the intracellular concentration, which, like sodium and potassium, contributes to a concentration gradient across the cell membrane. Also, the chloride ion is a co-factor in an enzyme reaction within neutrophils responsible for killing ingested microorganisms.

Virtually any source of chloride ions can be utilized, but it is preferred that the chloride ion source be reasonably soluble in water, chemically compatible with other components of the composition and nontoxic.

Nonlimiting examples of a source of anions to provide the chloride anion are sodium chloride, potassium chloride, calcium chloride, magnesium chloride, hydrochloric acid and ammonium chloride, with sodium chloride, potassium chloride, calcium chloride and magnesium chloride being preferred and with sodium chloride, potassium chloride and calcium chloride being most preferred.

Phosphate ions are a constituent of the major intracellular buffer system. Phosphate ions are also a component of many enzyme systems, and play a major role in intermediary metabolism and energy transfer within cells.

Virtually any source of phosphate ions can be utilized, but it is preferred that the phosphate ion source be reasonably soluble in water, chemically compatible with other components of the composition and nontoxic.

Nonlimiting examples of a source of anions to provide the phosphate anions are potassium phosphates, sodium phosphates, calcium phosphate (monobasic), and magnesium phosphate, with potassium phosphates and sodium phosphates being preferred and with potassium phosphates being most preferred.

Bicarbonate ions are also a major contributor to the osmolality of extracellular fluids. Also, the carbon dioxide-bicarbonate buffer system is the major buffer system in extracellular fluids.

Virtually any source of bicarbonate ions can be utilized, but it is preferred that the bicarbonate ion source be reasonably soluble in water, chemically compatible with other components of the composition and nontoxic.

Nonlimiting examples of a source of anions to provide the bicarbonate anions are sodium bicarbonate and potassium bicarbonate, with sodium bicarbonate being preferred.

Sulfate ions produce a buffering effect by associating with free hydrogen ions.

Virtually any source of sulfate ions can be utilized, but it is preferred that the sulfate ion source be reasonably soluble in water, chemically compatible with other components of the composition and nontoxic.

Nonlimiting examples of a source of anions to provide the source of sulfate anions are sodium sulfate, magnesium sulfate and calcium sulfate. Magnesium sulfate-heptahydrate is the preferred source of sulfate ions.

It is preferred that the source of cations and source of anions be provided by a single compound, e.g., sodium chloride or sodium sulfate. Of course, when one compound can be both the source of cations and the source of anions, one should attribute the amount of such source to both the source of cations and the source of anions. For example, if X amount of source of cations and X amount of source of anions are required, and one compound is both the source of cations and the source of anions, then only X, and not 2X, amount of such compound is required.

It is preferred that the source of cations be present in an amount of from about 0.35 to about 33, preferably from about 0.8 to about 17 and more preferably from about 1.5 to 15 percent by weight of the composition and that the source of anions be present in an amount of from about 0.25 to about 25, preferably from about 0.5 to about 13 and more preferably from about 1 to about 12 percent by weight of the composition.

In a particularly preferred embodiment, the composition of the present invention provides a source of cations to provide the cations sodium, potassium, magnesium and calcium and a source of anions to provide the anions chloride, sulfate, phosphate and bicarbonate. In this embodiment, it is preferred that the source of the sodium cation be present in an amount of from about 0.0025 to about 18, more preferably from about 0.15 to about 9 and even more preferably from about 0.3 to about 8.4 percent by weight of the composition, the source of the potassium cation be present in an amount of from about 0.0035 to about 24, more preferably from about 0.20 to about 12 and even more preferably from about 0.39 to about 11 percent by weight of the composition, the source of the magnesium cation be present in an amount of from about 0.0030 to about 25, more preferably from about 0.15 to about 12.7 and even more preferably from about 0.30 to about 11.6 percent by weight of the composition, the source of the calcium cation be present in an amount of from about 0.002 to about 33, more preferably from about 0.13 to about 16.8 and even more preferably from about 0.25 to about 15.4 percent by weight of the composition, the source of the chloride anion be present in an amount of from about 0.0015 to about 15, more preferably from about 0.1 to about 7.5 and even more preferably from about 0.2 to about 6.9 percent by weight of the composition, the source of the sulfate anion be present in an amount of from about 0.004 to about 25, more preferably from about 0.25 to about 12.7 and even more preferably from about 0.50 to about 11.60 percent by weight of the composition, the source of the phosphate anion be present in an amount of from about 0.004 to about 19, more preferably from about 0.25 to about 9.8 and even more preferably from about 0.5 to about 9.0 percent by weight of the composition, and the source of the bicarbonate anion be present in an amount of from about 0.003 to about 11, more preferably from about 0.22 to about 5.2 and even more preferably from about 0.40 to about 4.7 percent by weight of the composition.

In such particularly preferred embodiment it is preferred that the salts utilized are those that provide both a cation and an anion of the compositions of the present invention, e.g., sodium chloride rather than sodium acetate. Also, it is preferred that such particularly preferred embodiment be prepared by utilizing sodium chloride, preferably from about 0.45 to about 0.85 percent by weight of the composition; potassium chloride, preferably from about 0.01 to about 0.03 percent by weight of the composition; calcium chloride, preferably from about 0.009 to about 0.02 percent by weight of the composition using calcium chloride dihydrate; magnesium sulfate, preferably from about 0.009 to about 0.02 percent by weight of the composition using magnesium sulfate heptahydrate; sodium bicarbonate, preferably from about 1.5 to about 3.0 percent by weight of the composition; and potassium phosphate, preferably from about 0.005 to about 0.01 percent by weight of the composition using monobasic potassium phosphate; or rather than potassium phosphate, sodium phosphate (containing phosphate in an equivalent amount to the phosphate contained in the corresponding amount of potassium phosphate); or rather than magnesium sulfate, magnesium chloride (containing magnesium in an equivalent amount to the magnesium contained in the corresponding amount of magnesium sulfate).

C. The Buffer System

The pH of the compositions of the present invention generally can be from about 4 to about 10, preferably from about 5 to about 8 and more preferably from about 6 to about 7.5. However, it is preferred that the pH of the composition be within the range of physiological pHs of the cutaneous surface or mucosal surface to which the composition is to be applied when such surface is in a healthy state. But, when a disease process or condition on the mucosal or cutaneous surface results in a pH that is outside the normal range of pH for that surface, the pH of the composition applied to that surface can be outside the normal range of pH for that surface, but in the opposite direction relative to the pH abnormality caused by the disease process, but such pH should still be from about 4 to about 10. For example, a composition used as an oral rinse for the prophylaxis of dental plaque and gingivitis, used when no disease process or condition exists on the oral mucosal surface or gingival mucosal surface, would be formulated with a pH within the normal range for the gingival mucosa and oral mucoasa. A composition formulated to treat a vaginal disease would be formulated with a pH to reflect the effect on normal vaginal mucosal pH of the specific disease; for example, Candida vulvovaginitis tends to raise the vaginal pH, so the composition for treating that condition is formulated with an acidic pH; an overgrowth of vaginal Lactobacilli lowers the pH, so the composition for treating that condition is formulated with an alkaline pH. The effects on the pH of surfaces and wounds produced by various diseases and conditions of those surfaces and wounds are known to those skilled in the medical and pharmaceutical arts, which permits an appropriate choice of pH for any given composition depending on the disease or condition and the surface to be treated by the composition. Thus, since the pH of a cutaneous surface and the various mucosal surfaces varies, the preferred pH of the composition of the present invention varies.

If the intracellular pH deviates too far from its normal range, all the metabolic activities of the cell are decreased. Chemical reactions within cells and outside cells generate products that alter pH, but cells have mechanisms and buffers to help regulate the pH. Phosphate is the major natural intracellular buffer and bicarbonate is the major natural extracellular buffer.

White blood cells, even in the blood, are highly dependent on the natural intracellular and natural extracellular buffer systems to help maintain their normal pH.

When the white blood cells are present on a mucosal or cutaneous surface, the white blood cells are in a "hostile" environment with respect to pH. They are deprived of the buffering capacity of the blood and are exposed to numerous chemicals produced by infections, inflammatory diseases and wound healing, each of which changes the pH of the white blood cells. The change of this extracellular pH puts a strain on maintaining intracellular pH. Thus, the white blood cells must expend energy that could be utilized for fighting infections and inflammatory diseases and healing activities to maintain their own pH. Thus, the performance of the white blood cells is significantly impaired.

Accordingly, the compositions of the present invention have a pH within a range that allows the white blood cells to function optimally and is compatible with the pH of the cutaneous surfaces and mucosal surfaces in a healthy state to which the composition is to be applied.

Accordingly, in view of all of the above, it is preferred that the pH of the compositions of the present invention be the following:

| pH Range | Surface |
| --- | --- |
| from about 4.5 to about 9.5 | cutaneous |
| from about 6.0 to about 8.0 | conjunctiva |
| from about 6.0 to about 8.0 | mucosal lining of eyelid |
| from about 5.5 to about 9.0 | nasal mucosa |
| from about 5.5 to about 9.0 | paranasal sinus mucosa |
| from about 4.0 to about 8.0 | vaginal mucosa |
| from about 4.5 to about 8.5 | gingivae |
| from about 5.0 to about 9.5 | ano-rectal mucosa |
| from about 4.0 to about 8.0 | cervical mucosa |
| from about 4.0 to about 8.5 | uretheral mucosa |
| from about 4.0 to about 8.5 | urinary bladder mucosa |
| from about 6.5 to about 9.0 | tracheal and bronchial mucosae |

The pH of the compositions of the present invention after it is made depends on the choice and amount of buffer. The pH can be adjusted to suit the intended use. This can be accomplished by utilizing appropriate amounts of pH lowering or pH raising buffer components.

It is believed that any buffer component can be utilized to adjust the pH of the composition to the desired pH so long as the buffer component is biologically compatible. Nonlimiting examples of pH lowering buffer components are acetic acid; citric acid, di-metal salts of citric acid; hydrochloric acid; glutamic acid; ammonium chloride; phosphate buffers such as ammonium biphosphate, sodium biphosphate, sodium acid phosphate and potassium acid phosphate.

If the pH of the compositions of the present invention need to be adjusted upwards, then this can be accomplished by utilizing lower amounts of the acidic components of the composition or utilizing pH raising buffer components. Nonlimiting examples of pH raising buffer components are sodium hydroxide, potassium hydroxide, calcium hydroxide, bicarbonate buffers such as sodium bicarbonate and potassium bicarbonate, tri-metal salts of citric acid such as tri-sodium citrate and tri-potassium citrate, and salts of acetic acid such as sodium and potassium acetate.

In a preferred embodiment, the compositions of the present invention have a buffer system comprising from about 0.4 to about 4.70 percent by weight of the composition of a bicarbonate, preferably sodium bicarbonate; from about 0.5 to about 9 percent by weight of the composition of a phosphate; preferably monopotassium dihydrogen phosphate; from about 0.05 to about 0.1 percent by weight of the composition of citric acid and from about 1.0 to about 2.0 percent by weight of the composition of acetic acid. Compositions comprising such a buffer system are particularly efficacious.

It should be noted that several components can be both a source of cations or a source of anions and a buffer component, e.g., a bicarbonate and a phosphate. Since it is believed that a molecule can, at the same time, be a source of cations or source of anions and a buffer component, when calculating levels of the source of cations or the source of anions and the buffer component, the amount of such source can be attributed to both the source of cations or source of anions and the buffer component. Thus, if, for example, the composition requires X amount of a source of cations and X amount of the buffer component, then only X amount of the compound that can be a source of cations and a buffer component, not 2X amount of such compound, is required.

In addition, it is particularly preferred that the compositions of the present invention contain from about 0.5 to about 5.0 and preferably from about 1 to about 2 percent by weight of the composition of acetic acid or salt thereof (containing acetate in an equivalent amount to the acetate contained in the corresponding amount of acetic acid), for example, sodium acetate and potassium acetate. Acetic acid or salts thereof plays a role not only as a buffer component but also as an energy source. For example, when acetic acid was removed from the composition and another pH lowering buffer component (hydrochloric acid—not an energy source) was utilized to adjust the pH to the same value, the biological activity of the composition, as measured by the modified NBT Neutrophil Reduction Test, decreased by about 11%.

It should be noted that since it is believed that the primary role of acetic acid is that of a buffer, when calculating levels of acetic acid buffer required in the composition, one should attribute the acetic acid that is in excess of that required as a buffer to be attributed to the energy source.

D. Osmolality

Osmotic pressure is a main cause for the movement of water across cell membranes and is defined as the hydrostatic pressure needed to stop the net flow of water across a membrane, e.g., a cell membrane. The osmotic process occurs because there is a physical and chemical tendency for solutions on different sides of a semipermeable membrane to try to have the same concentrations of solutes in them.

White blood cells function optimally in a fluid environment that has an osmolality equivalent to that of blood serum. The normal osmolality of human blood serum is from about 289 to about 308 milliosmoles per kilogram water.

The osmolality of the compositions of the present invention is from about 140 to about 2000 milliosmoles (mOsm) per kilogram and preferably from about 675 to about 825 milliosmoles per kilogram. Of course, such osmolality is measured per kilogram of the base of the composition, e.g., water, ethyl alcohol or oleic acid. At such an osmolality the compositions of the present invention are most efficacious. It should be noted that this osmolality is higher than that of blood serum, but this is to allow for the dilution of the compositions of the present invention that occurs when the compositions are applied to a mucosal surface or cutaneous surface.

In the most general sense, the osmolality of the compositions of the present invention can be regulated by changing the amounts of any of all components.

In a specific sense, the most practical method of regulating the osmolality is to change the amount of single or multiple chemical components (normally present in a large enough amount to allow varying the osmolality over a sufficient range) whose alteration(s) will not significantly affect either the stability, the efficacy, or the other physical-chemical properties (pH, viscosity) of the composition.

Based on these criteria, it is preferred to regulate the osmolality by varying the amount of the source of anions and/or source of cations, e.g., sodium chloride. It is present in adequate amounts to allow varying the osmotic pressure over a sufficient range for various compositions. Varying amounts of, for example, sodium chloride over the necessary range does not significantly affect the stability, the efficacy, the pH, or the viscosity of the composition. Any of the other chemical components can be varied to adjust the osmolality, but sodium chloride is preferred.

In performing an adjustment of the osmolality, a theoretical calculation may be performed to predict the osmolality based on the amounts of the chemical components in the composition. This is useful for an initial estimate, however, using an osmometer to measure osmolality is the method of choice. Osmometers are standard, reliable, and relatively easy to operate instruments, which give actual measurements that allow determination of the osmolality of the formulation of compositions with high precision.

E. The Form Of The Compositions

The compositions of the present invention can be in virtually any form, for example, a solution, suspension or emulsion, with a solution being preferred. Thus, for example, the compositions can be a liquid, lotion, gel, ointment, cream, paste or salve. Also, of course, the compositions can be in the form of a powder that is treated to form a solution, emulsion or suspension immediately prior to use.

Any solvent can be utilized to form the solution, but, of course, it is preferred that the solvent be nontoxic. Nonlimiting examples of solvents include water, ethyl alcohol, glycerol and propyline glycol, with water being preferred.

In a preferred embodiment, the compositions of the present invention have a viscosity of at least about 5 centipoise, more preferably at least about 30 centipoise and even more preferably from about 35 centipoise to about 500,000 centipoise. The viscosity should be adjusted to be appropriate: for the surface to which the composition is to be applied, for the method of application and for the use on that surface. For example, the composition of the subject invention in the form of a nasal spray should be "thin" enough to pass through an atomizer, yet be more viscous than water so that the composition will adhere to the nasal mucosal surface. On the other hand, the composition of the present invention in the form for the treatment of a herpes simplex virus lesion, should be viscous enough to remain on the lesion for an extended period of time. Thus, the viscosity can be adjusted to allow the composition to adhere to the surface to which the composition is applied. For example, a composition more viscous than water will remain on a mucosal surface or cutaneous surface longer than if the viscosity of the composition were the same as that of water. Also, such an adjustment of the viscosity to mimic that of the mucosal surface, e.g., vaginal mucus, nasal mucus and saliva is preferred. All of this provides an optimal environment for the white blood cells, epithelial cells and fibroblasts, thereby permitting these cells to be optimally effective.

A viscosity increasing agent can be utilized to increase the viscosity of the compositions of the present invention. It is believed that the use of a viscosity increasing agent is especially preferred when the composition is a solution. In contrast, it is believed that other forms, e.g., suspensions and emulsions, result in the compositions of the present invention being quite viscous and, therefore, a viscosity increasing agent is not as apt to be necessary.

Any viscosity increasing agent can be utilized so long as it is biocompatible and non-toxic. Preferred viscosity increasing agents are water-soluble polymers. It is preferred that the water-soluble polymers have a molecular weight of from about 2,000 daltons to about 4,000,000 daltons. Nonlimiting examples of water-soluble polymers include cellulose ethers, dextran, polyvinyl pyrrolidone, gelatin, polyvinyl alcohol, polyalginic acid—preferably the sodium salt, polyacrylic acid—preferably the sodium salt, calcium polycarbophil and carboxy polymethyline, with the cellulose ethers being preferred. The preferred cellulose ether polymers are carboxymethylcellulose—preferably the sodium salt—hydroxyethylcellulose, methylcellulose, hydroxypropyl methylcellulose, hydroxypropyl cellulose, and hydroxybutyl methycellulose, with carboxymethylcellulose being preferred.

The viscosity of the compositions of the present invention can also be adjusted by formulating the compositions as suspensions or emulsions. It is believed that any base for a suspension or an emulsion can be utilized, so long as it is nontoxic. Nonlimiting examples of chemical components that can function as bases in suspensions or emulsions include petrolatum, oleic acid, olive oil, paraffin, cetyl esters wax, starch, beeswax, anhydrous lanolin, cetyl alcohol, stearic acid, glyceryl monostearate, polyethylene glycol, polyoxyl 40 stearate and polysorbates. Also, in order to assist in the stability of the suspension or emulsion, a suspending agent or emulsifying agent can be utilized. It is believed that any suspending agent and emulsifying agent can be utilized, so long as it is nontoxic. Nonlimiting examples of suspending agents or emulsifying agents include acacia, agar, alginic acid and sodium alginate, bentonite, carbomer, carageenan, cellulose, gelatin, polyvinyl alcohol, hydroxyethylcellulose, octoxynol 9, oleyl alcohol, providone, sodium lauryl sulfate and stearyl alcohol.

F. The Stabilization Of Certain Compositions Of The Present Invention

The compositions of the present invention that provide a source of cations to provide a cation selected from the group consisting of magnesium, calcium and mixtures thereof, and provide a source of anions to provide an anion selected from the group consisting of phosphate, bicarbonate and mixtures thereof and have a pH of from about 4 to about 10 have a stability problem in that insoluble precipitates of calcium and magnesium, as both phosphates and carbonates, can form. This severely reduces the shelf life and efficacy of such compositions of the present invention.

Accordingly, another aspect of the present invention is to overcome this stability problem.

It has been discovered that the compositions of the present invention that provide a source of cations to provide a cation selected from the group consisting of magnesium, calcium and mixtures thereof, and provide a source of anions to provide an anion selected from the group consisting of phosphate, bicarbonate and mixtures thereof and have a pH of from about 4 to about 10 and osmolality of from about 140 mOsm/kg to about 2,000 mOsm/kg can be stabilized by the addition of the appropriate amounts of a cellulose ether polymer and a chelating agent capable of contributing to the stabilization of such composition. This result is completely unexpected.

Nonlimiting examples of suitable chelating agents are citric acid, saccharic acid, ethylenediaminetetraacetic acid (EDTA), nitrilotriacetic acid (NTA), hydroxyethylenediamine-triacetic acid (HEEDTA), ethylenediaminedi [o-hydroxyphenylacetic acid] (EDDHA), ethyleneglycolbis (2-aminoethylether) tetraacetic acid (EGTA), diethylenetriaminepentaacetic acid (DTPA), 1,2-diaminocyclohexanetetraacetic acid (DCTA), N,N-bishydroxyethylglycine, and N-hydroxyethyliminodiacetic acid (HIMDA) and salts thereof, with citric acid, EDTA and salts thereof being preferred.

Any cellulose ether polymer can be utilized and preferably such polymer has a molecular weight of from about 50,000 daltons to about 1,000,000 daltons. The same cellulose ether polymers that can be utilized as viscosity enhancing agents can be utilized to stabilize the composition, i.e., carboxymethylcellulose—preferably the sodium salt—hydroxyethylcellulose, methylcellulose, hydroxypropyl methylcellulose, hydroxypropyl cellulose, and hydroxybutyl methycellulose, with carboxymethylcellulose being preferred.

The level of chelating agent that must be present to stabilize the composition is such that the molar ratio of the chelating agent to the total number of moles of the calcium ions plus magnesium ions is such that the composition results in no greater than about a 10% by weight decrease in the calcium plus magnesium concentration present after four weeks of storage at 42° C. when the composition is formulated as an aqueous solution to have a pH of about 4, and preferably about 7, and an osmolality of about 140 mOsm/kg and preferably about 750 mOsm/kg, i.e., no greater than about a 10% by weight of the calcium plus magnesium ions form precipitates. Thus, it should be noted that such composition can be a powder such that when the powder is formulated as such aqueous solution, the solution is stable.

This molar ratio can be readily determined experimentally. For example, for the chelating agent citric acid, such molar ratio is at least about 2 and for EDTA such molar ratio is at least about 1. Thus, generally such molar ratio is from about 1 to about 5.

It should be noted that citric acid and certain salts thereof in the composition of the present invention can be not only a chelating agent but also a buffer component and an energy source. Since it is believed that a molecule of citric acid or certain salts thereof can, at the same time, behave as a chelating agent and a buffer component, when calculating levels of chelating agent and buffer in the composition, the amount of citric acid or certain salts thereof can be attributed to both the chelating agent and buffer component. Thus, if the composition requires X amount of chelating agent and X amount of buffer, then only X amount of citric acid or certain salts thereof, rather than 2X amount of citric acid or certain salts thereof, is required. However, with respect to citric acid or certain salts thereof as an energy source, one should attribute the citric acid or certain salts thereof above that required as a buffer or chelating agent as an energy source. Thus, if the composition requires X amount of an energy source, X amount of a chelating agent and X amount of a buffer, then 2X amount of citric acid or certain salts thereof is required.

The level of cellulose ether polymer that must be present is not believed to be critical and it is preferred that the level is such that the viscosity of the composition is at least about 5 centipoise, preferably at least about 30 centipoise and more preferably from about 35 to about 500,000 centipoise.

The methods of the present invention can be utilized to treat any mammal, including humans, dogs, cats, cows and pigs, but, of course, the greatest value is for humans.

G. Mode Of Administration

The compositions of the present invention are utilized by contacting the mucosal or cutaneous surface that is to be treated, i.e., all of the compositions of the present invention are topically applied to the area being treated. Since the compositions of the present invention are extremely safe, the dosage and frequency of use of such compositions are not critical and, therefore, the compositions can be utilized at virtually any dose and frequency until the treatment or prevention is accomplished. In fact, animal toxicology studies indicate that even oral ingestion of the composition produced no adverse reactions. Thus, the composition can be applied in a one time application or even every hour for a period of days or even several times daily for a period of months. For example, the composition can be utilized for a period of several months to treat human papillomavirus or daily as a mouthrinse to treat gingivitis and prevent plaque. However, depending on the mucosal or cutaneous surface and the condition being treated or prevented, as described below, there are preferred modes and forms of administration. The forms can be liquid (viscosity less than about 50 centipoise and preferably less than about 35 centipoise), viscous-liquid (viscosity from about 50 centipoise to about 2,000 centipoise and preferably from about 75 centipoise to about 1,500 centipoise) and viscous (viscosity at least about 2,000 centipoise and preferably from about 2,500 centipoise to about 500,000 centipoise).

The compositions of the present invention need not be removed from the surface to which they were applied. After application, it is preferred that the composition remain undisturbed for at least about one hour. For example, no food or drink should be taken at least one hour after using oral compositions. This ensures that the chemical components of the composition remain in close proximity to white blood cells, epithelial cells and fibroblasts, thereby permitting the compositions to produce the desired benefit.

Also, it should be noted that the solvent of the composition tends to be absorbed or evaporate. Most of the chemical components of the composition are metabolized and/or absorbed. The viscosity enhancing agent is inert, but tends to be washed away by the action of body fluids and/or ordinary hygiene procedures, e.g., bathing.

In embodiments that require repeated application of the compositions of the present invention, one can wash the surface, with, for example, soap and water, if a build-up of residue from the composition is noted.

1. Ophthalmic

Similar forms, schedules of application, and methods of application can be used for application to the conjunctiva and mucosal lining of the eyelid.

Viscous-liquid compositions are preferred and liquid compositions are more preferred and can be applied as drops ("eyedrops"), or as an irrigant ("eyewash"). Eyedrops are dispensed from a dropper (glass or plastic), a dropping bottle (plastic), or a dropping container (plastic).

Viscous-liquids and liquids can also be sprayed onto the eye surface, although this is not a preferred method of application. Viscous-liquids and liquids can also be applied with an absorbant-tipped applicator (cotton, rayon, etc.), or by using small pieces of cotton (pledgets) that are soaked with the composition and placed in the conjunctival sac (sac formed by the lower eyelid).

Preferred dosage ranges are from about 1 to about 2 drops (about 0.25 ml to about 0.50 ml) one time per day upward (e.g., every hour for as long as needed). For irrigation, the preferred dosage is from about 5 ml. to about 50 ml. of liquid, and is a lower frequency dosage form than drops. Irrigation can be performed from about 1 to about 3 times daily and supplemented by drops if more treatment is necessary.

Viscous forms of the compositions (gels, ointments, etc.) can be applied according to the same dosage schedules as liquids, though the increased viscosity produces longer contact time, thereby requiring less frequent application. The viscous compositions can be contained in tubes or flexible containers from which the composition is squeezed, either directly inside the lower eyelid, or into an applicator which, in turn, dispenses the composition inside the lower eyelid. A column of the viscous composition of from about 0.25 to about 0.50 inches in length is the normal dosage; a weight range of from about 0.1 g. to about 50 g. (high dose for eye burn treatment) covers most uses.

For treatment of wounds (including burns), the compositions can be applied until healing has occurred (usually several weeks). For irritation and inflammation (e.g., associated with allergic reactions), the compositions can be applied until the irritation and/or inflammation has resolved. For dry-eye syndromes, the compositions can be applied until the syndrome resolves, or, on a chronic basis if the syndrome is non-resolving.

2. Nasal and Paranasal Sinus Mucosae

Similar viscous-liquid and liquid compositions are used for application to the nasal mucosal surfaces and the mucosal surfaces of the paranasal sinuses.

Viscous-liquid and liquid compositions can be administered as drops, sprays or irrigants. An absorbant nasal tampon (e.g., cotton, rayon, etc.) can be saturated with the liquid composition and inserted into the nostril.

Preferred dosages are from about 0.25 ml. to about 10 ml. (drops & sprays) or from about 50 ml. to about 250 ml. (irrigant).

Drops can be applied with a dropper (glass or plastic), or from a dropper bottle (plastic). Sprays can be applied from a squeeze bottle (plastic) or with a set-volume sprayer (plastic) attached to a glass or plastic bottle. Irrigants can be applied from a glass or plastic container or a flexible rubber syringe or dispensing bag through a nasal catheter (plastic or rubber).

Viscous forms of the compositions can also be utilized and include gels, ointments, creams, lotions, salves, etc. These viscous compositions can be applied by directly dispensing from a container (e.g., squeezing from a flexible tube or package), by application with a soft-tipped applicator (cotton, rayon, etc.), or by coating a cotton or rayon nasal tampon and inserting it into the nostril. Viscous compositions are less preferred for use in the paranasal sinuses than are liquid compositions.

For the treatment of wounds, including burns, the compositions can be applied until healing has occurred (usually several weeks), applied three or more times per day. For the treatment of irritation and inflammation due to the common cold, hay fever, influenza and other upper respiratory infections, sinusitis, other respiratory allergies, and environmental irritants, the compositions can be applied until the irritation and/or inflammation subsides. Dosage is performed on an as-needed basis, and the compositions can be applied as frequently as hourly.

The compositions are safe enough to be used continuously for chronic problems (chronic nasal allergies), and can be used prophylactically (e.g., during "allergy season").

3. Urinary Bladder Mucosa

Radiation therapy treatments (for cancer) administered to the pelvic region of the body can cause a painful inflammation, with tissue damage, of the mucosa of the urinary bladder; this condition is called radiation cystitis. For the treatment of this condition, a liquid composition is preferred and a viscous-liquid composition is particularly preferred.

The preferred dosage of the composition is from about 30 ml. to about 80 ml. (average about 50 ml.) of the viscous-liquid composition, administered through a urethral catheter into the urinary bladder. Initially, the composition is administered once per day, starting at the same time that the pelvic radiation therapy treatments start.

Treatments can be continued for up to several months after the completion of radiation therapy; the frequency of the treatments can be decreased (to once every 2 to 4 days).

A similar treatment regimen and dosage schedule can be used to promote healing and reduce discomfort after surgical procedures that are performed on the urinary bladder.

4. Cutaneous Surfaces

Compositions for application to the skin and vulva can be in liquid, viscous-liquid or viscous form.

Liquid and viscous-liquid compositions for application to the skin are preferred to be more viscous than eyedrops or nasal sprays, to promote better adhesion and longer contact. Liquid and viscous-liquid compositions can be applied directly from a bottle or container by pouring or using an applicator (cotton ball, cotton-tipped applicator, sponge, gauze sponge, etc.). Wound dressings, such as gauze bandages, gauze covered cotton pads, etc., can be wetted with a liquid or viscous-liquid composition and applied to a cutaneous surface when high saturation and long contact time are desired.

Liquid and viscous-liquid compositions can also be sprayed onto the skin when large areas are being treated (e.g., sunburn).

Dosage schedules, as on other surfaces, can range from a single application to hourly application for extended periods.

Preferred dosages for liquid and viscous-liquid compositions range from about 0.5 ml. to about 250 ml. in that such range covers most cutaneous conditions.

Viscous forms of cutaneous compositions include gels, lotions, creams, salves, ointments, etc.

Preferred dosages for viscous compositions range from about 0.5 gm. to about 250 gm. in that such range will treat most cutaneous conditions.

An exception to these dosage ranges occurs in a situation in which it is desirable to immerse a body part in a liquid composition—for example, immerse a burned hand in a tank of the composition, or immerse (bathe) the body of a child with chicken pox in the composition. In such cases, large volumes of the liquid compositions can be used as needed for these applications.

For treatment of wounds (including burns), the compositions can be applied frequently until healing has occurred— hourly for the first several days, then about 4 to about 6 times/day for one to two weeks, then about 2 to about 3 times/day until healing is complete. The compositions do not interfere with the use of antibiotics and other medications normally indicated. The compositions are made in a sterile manner—sterile applicators, bandages, gauze pads, etc. are indicated in the treatment of wounds with the compositions.

The compositions can be applied to decubitus ulcers (bed sores) and other non-healing wounds more frequently and for a longer period of treatment than for other types of wounds. The methods of application and the dosages are similar.

Cutaneous ostomy sites (e.g., colostomy, jejunostomy, etc.) are also treated as non-healing wounds.

Additional cutaneous conditions treated by the compositions are the cutaneous lesions produced by certain viral and fungal infections: herpes simplex virus [types 1 and 2] (e.g., cold sores, genital herpes, etc.), herpes zoster virus (shingles), varicella zoster virus (chicken pox), human papillomavirus (genital warts; condyloma acuminatum), and cutaneous Candida (fungal) infections. Liquid, viscous-liquid and viscous forms of the compositions can be used to treat these conditions. Direct application of from about 2 to about 6 times per day for up to several weeks, in sufficient amount to cover these lesions, is a preferred dosage.

5. Oral and Gingival Mucosae

All forms of the compositions of the present invention can be used in the oral cavity. The preferred forms are a liquid form (oral rinse; mouth wash), and a viscous form (toothpastes).

The preferred dosage of the liquid form is from about 5 ml. to about 25 ml. and preferably from about 10 ml. to about 20 ml., taken into the mouth and retained for about ½ to 2 minutes (with rinsing action), then expectorated. This is the simplest, easiest, and most universally usable dosage form for the oral compositions. The dosage can range from a single application to hourly rinsing for a prolonged period.

The dosage for viscous forms ranges from about 0.5 gm. to about 25 gm., which is applied directly from a container, or applied with an applicator swab, toothbrush, etc.).

It is preferred that no food or drink be taken for at least about one hour after the composition is applied.

For the prophylaxis of dental plaque (and gingivitis), it is preferred that the compositions be applied from about 1 to 2 times per day, every day to every other day, on an ongoing basis. For the treatment of overt, active gingivitis, it is preferred that the compositions be used from about 1 to about 6 times per day, every day, until the inflammation resolves.

For the treatment of oral wounds, it is preferred that the compositions be applied from about 1 to about 6 times per day, every day, until healing occurs.

For the treatment of oral viral infections, e.g., lesions due to herpes simplex virus, herpes zoster virus, or varicella zoster virus, it is preferred that the compositions be applied up to once every hour, until the lesions heal.

For the treatment of the oral effects of systemic cancer chemotherapy and for the treatment of the oral effects of antidepressant medications (both can produce a dryness, irritation, and discomfort secondary to altered saliva production), it is preferred that the composition be used from about 1 to about 6 times daily, as needed, until saliva production returns to normal.

For the treatment of the effects of head and neck radiation therapy (for cancer) on the oral mucosal tissues—severely altered salivary production, drying and fissuring of the oral mucosal tissues, radiation mucositis—it is preferred that the composition be applied up to once per hour, starting concurrently with the radiation therapy treatments, and continued for up to several months after the completion of radiation therapy.

Patients receiving systemic cancer chemotherapy, and AIDS patients, can develop oropharyngeal Candida infections (thrush). For the treatment of thrush, it is preferred that the composition be applied, alone or in combination with antifungal medications, up to once per hour until the infection resolves.

6. Tracheal and Bronchial Mucosae

Liquid forms of the composition are preferred and can be used in the types of respiratory care equipment that utilize fluids in their operation—e.g., nebulizers and inhalers.

The dosage amounts and schedules are the same as that used for other fluids used in these devices. Indications for usage are obstructive, inflammatory and infectious conditions that require therapy with respiratory care equipment.

7. Ano-Rectal Mucosa

The compositions can be used to treat several types of disease conditions of the ano-rectal mucosa.

Radiation therapy treatments to the pelvic region of the body can cause painful inflammation and tissue damage to the ano-rectal mucosa, known as radiation proctitis. It is preferred that a viscous-liquid composition be administered as a retention enema in a volume of from about 50 ml. to about 300 ml. The composition can be administered daily, starting concurrently with radiation therapy, and continuing at least several weeks after the radiation therapy is terminated.

After anal and/or rectal surgery, viscous liquid forms and viscous forms (gels, ointments, etc.) of the compositions can be applied to promote healing and reduce pain and discomfort. It is preferred that the compositions be applied from about 1 to about 10 times daily, with viscous-liquid compositions in amounts of from about 1 ml. to about 25 ml. and with viscous compositions in amounts of from 1 gm. to about 25 gm., until healing occurs.

Anal itching (pruritis) and irritation can be treated with liquid, viscous-liquid or viscous forms of the compositions.

It is preferred that liquid and viscous-liquid compositions be applied in doses of from about 1 ml. to about 10 ml. and viscous compositions be applied in doses of from about 1 gm. to 10 gm. The compositions can be applied from about 1 to about 6 times daily, until the itching or irritation subsides. Similar dosages can be used to aid in the treatment of hemorrhoids.

The compositions can be applied directly from a dispensing bottle or tube, or with an applicator (cylindrical piston dispensing applicator, absorbant-tipped applicator, etc.).

8. Vaginal and Cervical Mucosae

The mucosal surfaces of the vagina and the uterine cervix are anatomically adjacent, and similar forms, schedules of application and methods of application can be used for application of the compositions to the vaginal mucosa and the cervical mucosa.

All forms of the compositions can be used to treat conditions of the vaginal mucosa and cervical mucosa. The preferred forms are viscous-liquid and viscous.

It is preferred that the liquid and viscous-liquid compositions be administered as a rinse (douche), in a volume of from about 50 ml to about 400 ml. Smaller volumes of liquid and viscous-liquid, from about 1 ml. to about 50 ml., can be administered from a syringe-type applicator. Liquid and viscous-liquid compositions can also be a administered using absorbant-tipped applicators and preferably in volumes of from about 1 ml. to about 10 ml.

The viscous forms of the compositions can be administered using absorbant-tipped applicators and preferably in amounts of from about 1 gm. to about 10 gm., or using cylindrical, piston applicators, and preferably in amounts of from about 10 gm. to about 50 gm.

For the treatment of Candida vulvovaginitis, the compositions can be applied from 1 to about 6 times per day for up to seven days (or longer if needed). A similar dosage regimen can be used for the adjunctive treatment (in combination with the appropriate antibiotics) of bacterial and chlamydial vulvovaginitis.

Wounds (including burns and wounds secondary to childbirth) can be treated with liquid, viscous-liquid and viscous forms of the compositions. The compositions can be applied initially from about 4 times per day to about once per hour for the first week, then from about 2 to about 10 times per day until healing has occurred. A similar dosage regimen can be used for the treatment of nonspecific cervicitis and hemorrhagic cervicitis.

The compositions can be used to treat mucosal lesions of herpes simplex virus (HSV) infections, and human papillomavirus (HPV) infections. The preferred dosage regimen for HSV is from about 0.5 ml. to about 10 ml. of liquid or viscous-liquid, or from about 0.5 gm. to about 10 gm. of viscous compositions, from about 1 to about 10 times per day, applied directly to the lesion(s), until the lesion(s) heal. The preferred dosage regimen for HPV is preferably from about 1.0 ml. to about 50 ml. of liquid or viscous-liquid, or from about 1.0 gm. to about 50 gm. of viscous compositions, applied directly to any discrete lesions and to large areas of adjacent mucosal surface, twice daily for 12 or more weeks (this refers to internal infection and lesions, not the external HPV caused warts—condylomata accuminata).

The very severe form of vaginitis seen in patients receiving pelvic radiation therapy for cancer can be treated with the same dosage regimens as those used for treating wounds. The compositions are started at the time radiation therapy is started, and are continued up to several months after the completion of radiation therapy.

Patients receiving systemic chemotherapy for cancer, and patients taking antidepressant medications, can experience vaginal dryness, irritation and inflammation. The compositions can be applied to these patients from about 1 to about 10 times per day, and are continued at least as long as the other medications are used—longer if necessary. From about 1 ml. to about 100 ml. of liquid or viscous-liquid, or from about 1 gm. to about 100 gm. of viscous compositions is sufficient for most of these applications.

EXAMPLES

Example I: Preparation of the Compositions of the Present Invention

The compositions of the present invention can be prepared by straightforward means that involve chemical mixing processes and sterilization and aseptic filling processes. The compositions are formulated from readily available (pharmaceutical grade) chemicals, which are combined using standard mixing vessels (tanks) and stirring and mixing apparatus.

The compositions are sterilized using heat (autoclaving or bulk sterilization). Sterilization is necessary because the compositions are very nutritious for microorganisms and preferably contain no preservatives. Preservatives can be used, but could interfere with the functioning of white blood cells, the very thing the compositions act to improve.

The compositions of the present invention can be prepared as follows:

1. A pharmaceutical grade formulating tank is cleaned and prepared.
2. Distilled, deionized water (pharmaceutical grade "Water for Injection") or other solvents or bases are run into the tank in proper volume. If viscosity enhancing agents that are polymers requiring wetting through a device called an eductor are used, the water is run into the tank (at the appropriate temperature for the polymer) through the eductor, and such polymer is added into the eductor to allow it to be properly wetted.
3. After adding the water (or other solvent or base) and viscosity enhancing agent, the tank's mixing device (usually a pharmaceutical mixer consisting of an electric motor with a shaft and impeller) is turned on, and the solution is mixed until the proper viscosity for this stage of the manufacturing is obtained (the microscopic polymer agglomerates have been sufficiently dissolved); viscosity is checked during the mixing to establish this.
4. The dry chemical components are then added to the liquid or base and mixed until all are in solution (or suspension). If the composition is to be bulk-sterilized (in the tank), the energy source is not added at this time. [Bulk sterilization requires keeping the composition at an elevated temperature for a period long enough to possibly chemically alter any energy source present in the composition (such as carmelization of dextrose)—a very undesirable result.]
5. After all the dry components have gone into solution (or suspension), the pH of the liquid is measured, and a buffer component, e.g., acetic acid, is added to adjust the pH to its desired value. The liquid is mixed for sufficient time to allow pH equilibrium to be reached.
6. The preferred packaging for all the compositions is unit (single) dose, sterile packaging. The next steps then involve the sterilization and packaging of the composition being manufactured. If the composition is to be terminally sterilized in its final package (such as a glass bottle), the final packages (containers) are filled to the proper volume, sealed, and subjected to terminal sterilization. For example, a sealed glasses bottle with 10–15 mL of liquid composition containing dextrose in it can be steam sterilized (autoclaved) at 250° F. for 30 minutes. A sterilization cycle with those time and temperature parameters will not damage (caramelize) the energy source (dextrose). Also, because the containers are sealed for terminal sterilization, the pH of the composition in them does not change significantly during sterilization.

When a composition of the present invention is subjected to bulk sterilization, the increased amount of time for which the composition must be held at an elevated temperature could damage (chemically alter the energy source contained in it. For example, 700 liters of the composition was sterilized at 255° F. for 20 minutes, with a heat-up time of 1½ hours and a cool-down time of over 2 hours. When tried with dextrose in the composition, the dextrose caramelized, producing a brown (tea-colored) composition with a foul smell, altered pH, altered viscosity, and greatly decreased activity.

Thus, when bulk sterilization (heating) is used, several chemical formulation procedures different from those used in terminal unit-dose sterilization are employed. The energy source is added to the mixing-sterilizing vessel through a sterilizing filter (0.22 micron pore size) after the composition in the mixing-sterilizing vessel has been sterilized and cooled down. Also, a final pH adjustment is performed by addition of a buffer component through a (0.22 micron pore size) sterilizing filter after the composition in the mixing-sterilizing vessel has been sterilized and cooled down.

This pH-adjusting step is generally necessary because many large capacity mixing-sterilizing vessels require venting-to-atmosphere during sterilizing, which produces an inconsistent pH change during sterilization from batch to batch of composition.

After completing the previous steps, the composition is filled into individual containers from the mixing-sterilizing vessel. This filling procedure is conducted according to either sterile or aseptic filling procedures, well known and standard in the pharmaceutical industry.

A large variety of container types is available for packaging the compositions. Materials include glass, plastic (polymer), and metal (foil). Configurations of the containers include, but are not limited to, screw-cap bottles, pop-top bottles, spray bottles, dropper bottles, squeeze bottles, squeeze tubes, tear-open squeeze packages, and dropper packages.

Many types of formulating (mixing and sterilizing) equipment, and filling and packaging equipment are known in the pharmaceutical industry and usable to formulate and package the compositions, according to sterile production methods with sterile or aseptic filling and preferably no preservative use.

In summary, the manufacturing methods for the compositions of the present invention are relatively basic and straightforward. The overall process, in schematic form, consists of:

1. combining the viscosity enhancing agent with the liquid solvent (e.g., water) or preparing the base (e.g., petrolatum) for suspension;
2. combining the dry chemical components with 1;

3. adjusting pH;
4. either unit-dose packaging and sterilizing in the final container, or bulk sterilizing and sterile or aseptic packaging in unit-dose packaging; and
5. quality control measurements, e.g., pH, osmolality, viscosity, etc.

Example II: Comparative Example of Stabilization of a Composition of the Present Invention A composition was prepared according to the following formulation:

| COMPOSITION A | |
|---|---|
| | g/1,000 ml. |
| Dextran (m.w. 75,000) | 24.114 |
| Dextrose | 4.809 |
| Sodium Chloride | 6.732 |
| Sodium Bicarbonate | 21.967 |
| Calcium Chloride | 0.133 |
| Potassium Chloride | 0.173 |
| Potassium Phosphate, Monobasic | 0.082 |
| Magnesium Sulfate Heptahydrate | 0.144 |
| L(+) Tartaric Acid | 1.850 |
| Distilled, Deionized Water | 1,000 ml. |
| pH = 7.1 | |
| Viscosity = 2.5 centipoise | |
| Osmolality = 1460 mOsm/kg | |

The nine (dry, solid) chemical components were added to the water and mixed until a clear solution was obtained. Composition A became unstable within about one week, by which time white solid matter began to precipitate. Chemical analysis showed decreasing concentrations of calcium and magnesium; the precipitates were insoluble salts (phosphates and carbonates) of calcium and magnesium.

A composition was prepared according to the formulation:

| COMPOSITION B | |
|---|---|
| Dextrose Monohydrate | 5.29 g. |
| Sodium Bicarbonate | 21.98 g. |
| Sodium Chloride | 6.73 g. |
| Calcium Chloride Dihydrate | 0.13 g. |
| Potassium Chloride | 0.17 g. |
| Monobasic Potassium Phosphate | 0.082 g. |
| Magnesium Sulfate Heptahydrate | 0.14 g. |
| Citric Acid | 0.72 g. |
| Carboxymethylcellulose (high viscosity; ave. m.w. 700,000) | 6.00 g. |
| Glacial Acetic Acid[1] | 14.6 ml. |
| Distilled, Deionized Water | 1,000 ml. |
| pH = 6.4 | |
| Viscosity = 35 centipoise | |
| Osmolality = 750 mOsm/kg | |

[1]The amount of glacial acetic acid was determined during the formulation process. Because of the variability of the pH produced by the other chemical components when dissolved in the water and the variability of the pH of the water, the amount of the glacial acetic acid added is determined by reading a pH meter placed in the composition during the formulation process. Thus, the amount added is dependent upon the desired resultant pH.

This composition, Composition B, which contains citric acid and carboxymethylcellulose, has shown chemical stability for over two years (no precipitate formation; stable concentration of calcium and magnesium). Composition B has also shown stable biological activity for over two years as demonstrated by the results of Example III.

Composition B is able to tolerate sterilization—bulk heat sterilization, when made according to Example I and unit-dose sterilization by autocalving—and remain stable.

Example III: The Modified NBT Neutrophil Reduction Test

A testing procedure, used as an indication of desired biological activity of the compositions of the present invention, uses a modification of an existing test known as the Nitroblue Tetrazolium (NBT) Neutrophil Reduction Test.

The NBT Neutrophil Reduction Test was first developed as an aid in differentiating febrile conditions that are bacteria-induced from those that are non-bacterial in origin. In bacterial infections, the percentage of neutrophils that are assessed as "positive" by the test is usually increased. The test can also be used as an aid in diagnosing defects of neutrophil function, such as chronic granulomatous disease and neutrophilic enzyme deficiencies, in which the percentage of "positive" neutrophils is decreased. See "The Nitroblue Tetrazolium (NBT) Test: A Simple, Reliable Method and a Review of Its Significance," *American Journal of Medical Technology*, Volume 40, Number 4, April 1974; and Nitroblue Tetrazolium (NBT) Reduction, Histochemical Demonstration in Neutrophils, Sigma Diagnostic Procedure No. 840.

A modified version of the NBT Neutrophil Reduction Test is utilized as an indicator of the biological activity of the compositions of the present invention. In this modified NBT test, neutrophils are obtained from human blood collected from donors with no known metabolic defects of neutrophil function, no systemic illness, which would interfere with the NBT test, and who are not taking any medications (such as steroids), which would alter neutrophil function. Compositions can then be tested by adding them to the blood used in the test and observing the effects of the formulation on the neutrophils. Two controls are tested simultaneously and their results are compared with the results of the composition tested.

Standard Test—The test involves incubation of human blood with a buffered solution of NBT. After a neutrophil phagocytizes NBT, an internal biochemical reaction reduces the NBT to formazan, which appears as large irregularly shaped dark purple to black intracytoplasmic inclusions. Smears are prepared, stained and examined microscopically to determine the percentage of neutrophils showing intracytoplasmic deposits of formazan (these cells are read as "positive").

Modified NBT Neutrophil Reduction Test—The test involves incubation of human blood mixed with a composition of the present invention, a buffered solution of NBT, and a Stimulant (Test Sample). A Reference Standard and a Control Standard are prepared with the buffered solution of NBT and Stimulant, and run simultaneously with the composition. Smears are prepared, stained and examined microscopically to determine the percentage of neutrophils showing intracytoplasmic deposits of formazan. The results for the Test Sample are compared to the results for the Standards.

Results of this Modified NBT Test are expressed as a percentage (which is the number of neutrophils out of each 100 counted which are "positive"). Increasing percentages indicate increasing activity of the compositions being tested.

The modified NBT Neutrophil Reduction Test has been used to compare the activity of the Composition A to Composition B of Example II. Though both compositions show significant increases in activity, as measured by such test, Composition B consistently showed higher activities than Composition A. Combined data from a series of 10 comparative runs of the test show these activities:

Composition A: 52.3±2.5 %
Composition B: 63.5±5.4 %

Example IV: Oral Post-Surgical Use

Two adult male patients underwent extensive gingival (gum) resection surgery, and both were advised by their respective periodontists that so much gum tissue was cut away, tissue grafting would be necessary. Each patient used the Composition A of Example II as a mouthrinse, three times daily for approximately one month. When each patient returned to his respective periodontist, there was great surprise and each patient was told that his gum tissue grew back abnormally well, and that tissue grafting would not be necessary.

This indicates the concept that the basic effects of the compositions of the present invention can contribute significantly to aiding the process of wound healing.

Example V: Nasal Inflammation Use

One adult male-patient, who regularly suffers from persistent, uncomfortable inflammation of the nasal mucosa during and after having a viral upper respiratory infection (cold), used the Composition A in Example II in the form of nosedrops. The patient claimed that the composition was the first medication he had ever used that relieved the pain and discomfort and alleviated the dripping (rhinorrhea) he always experienced after a cold.

One adult female patient, who regularly suffers from irritated, swollen, "cracked", occasionally bleeding tissue around her nasal openings during and after a cold, used Composition B of Example II in the form of nosedrops and applied it topically with cotton swabs. The patient claimed that the composition was the first medication that relieved her pain and discomfort, and did so within 24 hours. Healing of her visible nasal lesions was easily and clearly observed.

These two cases again support the concept that the compositions of the present invention contribute significantly to aiding the processes of wound healing and resolving ongoing inflammation.

Example VI: Candida Vaginitis Use

Over 50 patients, under close supervision by an OB/GYN M.D. and nurse, used the Composition A of Example II, applied topically with cotton swabs, twice daily for seven days, to treat Candida vulvovaginitis. Successful treatment was judged by significant reduction in symptoms (patient assessment) and total reduction of clinical signs—redness, swelling, discharge (physician assessment). The composition was applied both to the surface of the vaginal mucosa and to the (external) vulvar tissue. A high success rate, in excess of 80%, was obtained. Some successfully treated cases were unusually difficult—these patients had long-standing chronic recurrent vaginitis that did not respond well to existing vaginal antifungal medications. In addition, patients were very pleased with the aesthetics of the composition. Unlike existing vaginal antifungal medications, the composition was not "messy, greasy, slimy, runny, drippy" (patient's own words), it didn't soil the bed covers or stain underclothing, and it could be used during the work day. The greatest complaint was that the composition had to be measured and mixed with water before each use; most patients don't like doing "bathroom chemistry".

After finishing the aforementioned study using the Composition A, work was completed on chemical stability experiments, and a new, stable liquid composition was prepared specifically for vulvovaginal use. It had a lower pH than that of Composition A; the normal vaginal pH is as low as 4.0–5.5, Composition A had a pH of about 7.1 and the new vaginitis composition had a pH of 6.4. It also had a much higher viscosity than Composition A. The new composition is Composition B of Example II.

A pilot study was conducted on 30 adult female patients with Candida vulvovaginitis with Composition B. 29 of 30 (96.7%) of these patients were successfully treated using Composition B. Some of these patients had previously used Composition A, and felt that the new, stable liquid worked faster and better, felt better, and was much easier to use than Composition A.

Most of the aforementioned 30 patients had difficult, chronic-recurrent vaginitis, and it was actually surprising how well the composition worked. One patient, a woman in her 30's who had developed severe, almost constant Candida vulvovaginitis after prolonged antibiotic therapy necessitated by injuries sustained in an automobile accident, was unable to receive significant benefit from any of the prescription vaginal antifungal medications she used over a three year period. Composition B brought her almost immediate improvement, and after three courses of therapy over a three month period, her vulvovaginitis completely disappeared, and has not recurred since.

Although no formal attempt was made to collect recurrence data, patients have said that in their own perceptions, after using Composition B they had fewer recurrences, farther apart in time, which are less severe.

These over 80 clinical cases support the concept that the compositions contribute significantly to aiding the process of resolving an infectious disease process and restoring balance to a microbial ecologic system.

These clinical cases also point out the major clinical differences between Composition A and Composition B:

1. Chemical stability of Composition B allows more ease of use and greater patient acceptance; and
2. Although both worked clinically, Composition B was felt to be more effective (patient perceptions and physician observations) and more aesthetically pleasing (patient perceptions).

Example VII: Post Head and Neck Radiation Therapy Use [Oral]

An adult female patient with a brain tumor (unfortunately inoperable) received large doses of radiation therapy to her head and neck. A severe mucosal inflammation (mucositis) occurred, as expected with this type of treatment, in her oral mucosa and the mucosa of her throat. She rinsed and gargled with Composition A daily, and claimed that the dryness, pain, cracking, and bleeding were all relieved, nearly totally, within seven days.

This case supports the concept that the composition can aid in the process of wound healing—in this case the wounds were the changes caused by high-dose radiation therapy to mucosal epithelium.

Example VIII: Herpes Virus Therapy

Four adult patients, male and female, who suffer from recurrent "cold sores" (facial herpes simplex virus type-1)

applied Composition A topically (2–6 times per day) to their herpes lesions after outbreaks. All four patients claimed that the pain and discomfort of their herpes lesions were relived within 24 hours of application of Composition A, and that the lesions healed within 2 to 3 days. Two of these patients further claimed that when they applied Composition A at the first sign of an outbreak (tingling sensation, no physical lesion), the outbreak of the physical lesions was prevented.

A clinical pilot study was performed on 6 adult female patients who suffer from recurrent genital herpes (herpes simplex virus type-2). Under close supervision of an OB/GYN M.D. and a nurse, the six patients applied Composition A to their genital herpes lesions after the outbreak (topical application, 2–6 times per day). These patients had used Zovirax™ (acyclovir, one of the few currently approved prescription medications for treating herpes simplex) and were well aware of the normal course of their herpes lesions, treated and untreated. The following table summarizes the results of this pilot study:

|  | Symptom Relief (Cessation of localized pain/discomfort) | Significant Lesion Healing |
|---|---|---|
| Untreated | 7–10 days | 7–10 days |
| Zovirax | 5–7 days | 5–7 days |
| Composition A | 1 day | 2 days |

These results were unexpectedly good. The patients were very positive about the medication and the results of treatment.

An additional patient was treated with Composition A who had primary (first occurrence) genital herpes. Her symptoms were alleviated much more quickly than the OB/GYN usually noted in primary cases.

An adult male patient with recurrent shingles (herpes zoster virus) lesions on the lower extremity of his body used Composition A topically, 2–5 times per day, to treat an outbreak. This patient had previously used Zovirax™ on several occasions. He claimed that the pain and discomfort of the lesion resolved within two days and the lesions were significantly healed within two days. He claimed Zovirax™ made almost no difference when he used it; with or without Zovirax™ the lesions usually took several weeks to resolve.

These clinical cases support the concept that the compositions of the present invention contribute significantly to aiding the process of resolving acute outbreaks of herpes simplex virus, types 1 and 2, and herpes zoster. Thus, the compositions of the present invention will also significantly contribute to aiding the process of resolving other types of viral outbreaks and infections, because of the common elements of the immune response to viral infections.

Example IX: Human Papillomavirus (HPV) Use

The success in treating herpes simplex (type 1 and 2) and herpes zoster outbreaks indicated that the compositions of the present invention might be useful in treating other types of viral infections and lesions. A pilot clinical study on patients infected with (genital) human papillomavirus (HPV) was conducted.

There are more than 60 types of HPV identified, of which approximately 20 infect mucosal tissue. Two types are associated with benign anogenital warts (condyloma acuminatum); nine types are associated with cervical intraepithelial neoplasa (CIN) and carcinoma. HPV is both sexually and non-sexually transmitted and is already very prevalent (see Bauer et al., *JAMA*, 265(4), 472–477, Jan. 23/30, 1991); in one study, 46% of a group of 467 asymptomatic women seen for routine annual gynecological examination were positive for HPV infection. Unlike the herpes viruses, which travel from the skin through nerve fibers to ganglia and can remain latent until an active outbreak, HPV does not enter nerves. The virus tends to remain in epithelial cell layers. Current methods of therapy are directed at destroying the infected cells and include application of chemicals (concentrated trichloroacetic acid, 5-fluoruracil) and ablation of tissue using a laser. In addition to destroying HPV infected cells, these methods stimulate a generalized immune response in the treated areas, which some investigators believe contributes to the therapeutic effect of the treatments. These treatment methods are painful and produce lasting discomfort.

A pilot clinical study was performed using Composition A on adult female patients with genital HPV (lesions of the uterine cervix, vagina, and/or vulva). Composition A was used before any conventional treatment; it was applied topically, several times per day, for 4 to 13 weeks. Eight patients had Pap Smear and/or biopsy evidence of HPV infection. All eight patients had abnormal Pap Smears (of varying degrees of severity, from squamous atypia to moderate dysplasia). After treatment with Composition A, the Pap Smears of all eight patients became negative (and the repeat biopsies all showed improvements).

Composition A was used by two patients with genital warts (condylomata acuminata) caused by HPV. The two patients applied Composition A topically, 2 to 3 times per day, for 8 weeks. Physical examinations showed that in both cases the lesions had disappeared and repeat biopsies confirmed the absence of HPV/condylomata acuminata.

The results of this pilot study were beyond anyone's expectations. A composition of the present invention was able to reverse virally induced anatomic abnormalities, some of which were pre-malignant. These clinical cases support the concept that the compositions of the present invention contribute significantly to resolving HPV infections in epithelial membranes and thereby reversing anatomical abnormalities, some of which are pre-malignant, caused by HPV.

I claim:

1. A method for treating or preventing a condition in a mammal caused by the presence of a disease causing agent on a mucosal surface or a cutaneous surface wherein said disease causing agent can be diminished by the actions of the white blood cells of a mammal comprising contacting the mucosal surface or the cutaneous surface of said mammal in need of said treatment or prevention with an effective amount to treat or prevent said condition of a composition comprising:

(a) an energy source for white blood cells;

(b) a source of cations to provide a cation selected from the group consisting of sodium, potassium, magnesium, calcium and mixtures thereof; and (c) a source of anions to provide an anion selected from the group consisting of chloride, sulfate, phosphate, bicarbonate, and mixtures thereof;

wherein the pH of said composition is from about 4 to about 10 and the osmolality of said composition is from about 140 mOsm/kg to about 2,000 mOsm/kg; with the proviso that said mucosal surface is not the oral cavity.

2. The method of claim 1 wherein said mammal is a human.

3. The method of claim 2 wherein said mucosal surface is selected from the group consisting of conjunctiva, the mucosa of the inner surface of an eyelid, nasal mucosa, paranasal sinus mucosa, vaginal mucosa, urinary bladder mucosa, urethral mucosa, ano-rectal mucosa, cervical mucosa, tracheal mucosa and bronchial mucosa.

4. The method of claim 3 wherein said mucosal surface is the conjunctiva and said condition is selected from the group consisting of allergic conjunctivitis, nonspecific conjunctival irritation and inflammation and dry eye syndromes.

5. The method of claim 3 wherein said mucosal surface is the mucosa of the inner surface of the eyelid and said condition is selected from the group consisting of allergic conjunctivitis, nonspecific conjunctival irritation and inflammation and dry eye syndromes.

6. The method of claim 3 wherein said mucosal surface is the nasal mucosa and said condition is selected from the group consisting of irritation and inflammation due to a common cold, influenza, upper respiratory infections, hayfever, respiratory allergies and environmental irritants.

7. The method of claim 3 wherein said mucosal surface is the paranasal mucosal surface and said condition is selected from the group consisting of acute and chronic sinusitis, irritation and inflammation due to a common cold, influenza, upper respiratory infections, hayfever, respiratory allergies and environmental irritants.

8. The method of claim 3 wherein said mucosal surface is the vaginal mucosa and said condition is selected from the group consisting of fungal infections, viral infections, bacterial infections, protozoal infections, chlamydial infections, radiation vaginitis, dryness secondary to systemic chemotherapy for cancer, irritation secondary to systemic chemotherapy for cancer, inflammation secondary to systemic chemotherapy for cancer, dryness secondary to use of antidepressant medication, irritation secondary to use of antidepressant medication and inflammation secondary to use of antidepressant medication.

9. The method of claim 8 wherein said condition is selected from the group consisting of *Candida vulvovaginitis*, herpes simplex virus infections, herpes zoster virus infections and human papillomavirus infections.

10. The method of claim 9 wherein said condition *Candida vulvovaginitis*.

11. The method of claim 3 wherein said mucosal surface is the urethral mucosa and said condition is radiation urethritis.

12. The method of claim 3 wherein said mucosal surface is the ano-rectal mucosa and said condition is selected from the group consisting of viral infections, fungal infections, inflammations of hemorrhoids, anal pruritis and radiation proctitis.

13. The method of claim 3 wherein said mucosal surface is the cervical mucosa and said condition is selected from the group consisting of viral infections, fungal infections, protozal infections, chlamydial infections, nonspecific cervicitis and hemorrhagic infections.

14. The method of claim 13 wherein said condition is selected from the group consisting of human papillomavirus infections and herpes simplex virus infections.

15. The method of claim 3 wherein said mucosal surface is the urinary bladder mucosa and said condition is radiation cystitis.

16. The method of claim 3 wherein said mucosal surface is the bronchial mucosa or tracheal mucosa and said condition is selected from the group consisting of irritation or inflammation secondary to chronic tracheo-bronchitis, asthmatic tracheo-bronchitis and chronic obstructive pulmonary disease.

17. The method of claim 1 wherein said energy source is selected from the group consisting of metabolic intermediates involved in energy production, monosaccharides, oligosaccharides, polysaccharides, metabolizable lipids, amino acids, oligopeptides and metabolizable proteins.

18. The method of claim 1 wherein said energy source is selected from the group consisting of D-glucose, glucose-6-phosphate, fructose-6-phosphate, D-mannose, D-galactose, D-fructose, maltose, lactose, sucrose, glycogen, starch, fatty acids, neutral fats, pyruvic acid, lactic acid, citric acid and pharmaceutically acceptable salts thereof, and mixtures thereof.

19. The method of claim 18 wherein said energy source is D-glucose.

20. The method of claim 17 wherein said energy source is present in an amount of energy equivalent to D-glucose of from about 0.10 to about 10 weight percent D-glucose of the composition.

21. The method of claim 1 wherein said source of cations is selected from the group consisting of sodium chloride, potassium chloride, magnesium sulfate, calcium chloride and mixtures thereof.

22. The method of claim 1 wherein the source of anions is selected from the group consisting of sodium chloride, potassium chloride, calcium chloride, potassium phosphates, sodium bicarbonate, magnesium sulfate heptahydrate and mixtures thereof.

23. The method of claim 1 wherein the source of cations is present in an amount of from about 0.35 to about 33 percent by weight of the composition and the source of anions is present in an amount of from about 0.25 to about 25 percent by weight of the composition.

24. The method of claim 1 wherein said source of cations provides the cations sodium, potassium, magnesium and calcium and said source of anions provides the anions chloride, sulfate, phosphate and bicarbonate.

25. The method of claim 24 wherein said source of anions and said source of cations provide from about 0.45 to about 0.85 percent by weight sodium chloride, from about 0.01 to about 0.03 percent by weight of potassium chloride, from about 0.009 to about 0.02 percent by weight of calcium chloride dihydrate, from about 0.009 to about 0.02 percent by weight magnesium sulfate heptahydrate, from about 1.5 to about 3 percent by weight sodium bicarbonate and from about 0.005 to about 0.01 percent by weight potassium phosphate.

26. The method of claim 1 wherein said pH is from about 5 to about 8.

27. The method of claim 1 wherein said composition further comprises a buffer system comprising from about 0.4 to about 4.7 percent by weight of a bicarbonate, from about 0.5 to about 9 percent by weight of a phosphate, from about 0.05 to about 0.1 percent by weight of citric acid and from about 1.0 to about 2.0 percent by weight of acetic acid.

28. The method of claim 27 wherein said bicarbonate is sodium bicarbonate and said phosphate is monopotassium dihydrogen phosphate.

29. The method of claim 1 wherein said composition further comprises from about 0.5 to about 5.0 percent by weight of acetic acid or an equivalent amount of a salt thereof.

30. The method of claim 1 wherein said osmolality is from about 675 mOsm/kg to about 825 mOsm/kg.

31. The method of claim 1 wherein said composition has a viscosity of at least about 30 centipoise.

32. The method of claim 31 wherein said viscosity is from about 35 to about 500,000 centipoise.

33. The method of claim 1 wherein said composition further comprises a water-soluble polymer having a molecular weight of from about 2,000 to about 4,000,000 daltons.

34. The method of claim 33 wherein said water-soluble polymer is a cellulose ether polymer.

35. The method of claim 34 wherein the cellulose ether polymer is carboxymethylcellulose.

36. The method of claim 2 wherein said cutaneous surface is selected from the group consisting of skin and vulva.

37. The method of claim 36 wherein said cutaneous surface is skin and said condition is selected from the group consisting of herpes zoster virus infections, varicella zoster virus infections, cutaneous Candidiasis and human papillomavirus infections.

38. The method of claim 36 wherein said cutaneous surface is the vulva and said condition is selected from the group consisting of chronic vulvovestibulitis, herpes simplex virus infections, herpes zoster virus infections, varicella zoster virus infections and human papillomavirus infections.

39. The method of claim 1 wherein said composition is in a form selected from the group consisting of a solution, suspension and emulsion.

40. The method of claim 39 wherein said form is a solution and the solvent in said solution is water.

41. A method for healing a wound of a mucosal surface or cutaneous surface of a mammal comprising contacting the mucosal surface or the cutaneous surface of a mammal in need of said healing with a therapeutically effective amount of a composition comprising:

(a) an energy source for white blood cells;

(b) a source of cations to provide a cation selected from the group consisting of sodium, potassium, magnesium, calcium and mixtures thereof; and (c) a source of anions to provide an anion selected from the group consisting of chloride, sulfate, phosphate, bicarbonate and mixtures thereof;

wherein the pH of said composition is from about 4 to about 10 and the osmolality of said composition is from about 140 mOsm/kg to about 2,000 mOsm/kg.

42. The method of claim 41 wherein said mammal is a human.

43. The method of claim 42 wherein said mucosal surface is selected from the group consisting of conjunctiva, the mucosa of the inner surface of the eyelid, nasal mucosa, paranasal sinus mucosa, vaginal mucosa, urinary bladder mucosa, urethral mucosa, ano-rectal mucosa, cervical mucosa, tracheal mucosa, bronchial mucosa, oral mucosa and gingival mucosa.

44. The method of claim 43 wherein said mucosal surface is selected from the group consisting of the mucosa of the inner surface of the eyelid, nasal mucosa, paranasal sinus mucosa, uretheral mucosa, ano-rectal mucosa, tracheal mucosa, oral mucosa, gingival mucosa and bronchial mucosa and said wound is selected from the group consisting of surgical wounds, traumatic wounds and burns.

45. The method of claim 43 wherein the mucosal surface is the conjunctiva and said wound is selected from the group consisting of surgical wounds, traumatic wounds, burns and wounds associated with corneal grafting procedures.

46. The method of claim 43 wherein said mucosal surface is the vaginal mucosa and said wound is selected from the group consisting of surgical wounds, traumatic wounds, burns, wounds associated with childbirth and wounds associated with topical chemotherapy.

47. The method of claim 43 wherein said mucosal surface is the cervical mucosa and said wound is selected from the group consisting of surgical wounds, traumatic wounds, burns, wounds associated with childbirth and wounds associated with topical chemotherapy.

48. The method of claim 43 wherein said mucosal surface is the urinary bladder mucosa and said wound is selected from the group consisting of surgical wounds and traumatic wounds.

49. The method of claim 41 wherein said energy source is selected from the group consisting of metabolic intermediates involved in energy production, monosaccharides, oligosaccharides, polysaccharides, metabolizable lipids, amino acids, oligopeptides and metabolizable proteins.

50. The method of claim 41 wherein said energy source is selected from the group consisting of D-glucose, glucose-6-phosphate, fructose-6-phosphate, D-mannose, D-galactose, D-fructose, maltose, lactose, sucrose, glycogen, starch, fatty acids, neutral fats, pyruvic acid, lactic acid, citric acid and pharmaceutically acceptable salts thereof, and mixtures thereof.

51. The method of claim 50 wherein said energy source is D-glucose.

52. The method of claim 49 wherein said energy source is present in an amount of energy equivalent to D-glucose of from about 0.10 to about 10 weight percent D-glucose of the composition.

53. The method of claim 41 wherein said source of cations is selected from the group consisting of sodium chloride, potassium chloride, calcium chloride, magnesium sulfate and mixtures thereof.

54. The method of claim 41 wherein said source of anions is selected form the group consisting of sodium chloride, potassium chloride, calcium chloride, potassium phosphates, sodium bicarbonate, magnesium sulfate heptahydrate and mixtures thereof.

55. The method of claim 41 wherein said source of cations provides the cations sodium, potassium, magnesium and calcium and said source of anions provides the anions chloride, sulfate, phosphate and bicarbonate.

56. The method of claim 55 wherein said source of anions and said source of cations provide from about 0.45 to about 0.85 percent by weight sodium chloride, from about 0.01 to about 0.03 percent by weight of potassium chloride, from about 0.009 to about 0.02 percent by weight of calcium chloride dihydrate, from about 0.009 to about 0.02 percent by weight magnesium sulfate heptahydrate, from about 1.5 to about 3 percent by weight sodium bicarbonate and from about 0.005 to about 0.01 percent by weight potassium phosphate.

57. The method of claim 41 wherein the source of cations is present in an amount of from about 0.35 to about 33 percent by weight of the composition and the source of anions is present in an amount of from about 0.25 to about 25 percent by weight of the composition.

58. The method of claim 41 wherein said pH is from about 5 to about 8.

59. The method of claim 41 wherein said composition further comprises a buffer system comprising from about 0.4 to about 4.7 percent by weight of a bicarbonate, from about 0.5 to about 9 percent by weight of a phosphate, from about 0.05 to about 0.1 percent by weight of citric acid and from about 1.0 to about 2.0 percent by weight of acetic acid.

60. The method of claim 59 wherein said bicarbonate is sodium bicarbonate and said phosphate is monopotassium dihydrogen phosphate.

61. The method of claim 41 wherein said composition further comprises from about 0.5 to about 5.0 percent by weight of acetic acid or an equivalent amount of a salt thereof.

62. The method of claim 41 wherein said osmolality is from about 675 mOsm/kg to about 825 mOsm/kg.

63. The method of claim 41 wherein said composition has a viscosity of at least about 30 centipoise.

64. The method of claim 63 wherein said viscosity is from about 35 to about 500,000 centipoise.

65. The method of claim 41 wherein said composition further comprises a water-soluble polymer having a molecular weight of from about 2,000 to about 4,000,000 daltons.

66. The method of claim 65 wherein said water-soluble polymer is a cellulose ether polymer.

67. The method of claim 66 wherein said cellulose ether polymer is carboxymethylcellulose.

68. The method of claim 42 wherein said cutaneous surface is selected from the group consisting of skin and vulva.

69. The method of claim 68 wherein said cutaneous surface is skin and said wound is selected from the group consisting of surgical wounds, traumatic wounds, burns and wounds associated with skin grafting procedures.

70. The method of claim 68 wherein said cutaneous surface is the vulva and said wound is selected from the group consisting of surgical wounds, traumatic wounds, burns and wounds associated with skin grafting procedures.

71. The method of claim 41 wherein said composition is in a form selected from the group consisting of a solution, suspension and emulsion.

72. The method of claim 71 wherein said form is a solution and the solvent in said solution is water.

73. A composition comprising:
(a) a source of cations to provide a cation selected from the group consisting of magnesium, calcium and mixtures thereof;
(b) a source of anions to provide an anion selected from the group consisting of phosphate, bicarbonate and mixtures thereof;
(c) a chelating agent capable of contributing to the stabilization of said composition; and
(d) a cellulose ether polymer;
wherein the molar ratio of said chelating agent to the total numbers of moles of said calcium cations plus said magnesium cations is such that said composition results in no greater than about a 10% by weight decrease in the calcium plus magnesium concentration in said composition after four weeks of storage at 42° C. when the composition is formulated as an aqueous solution to have a pH of about 4 and an osmolality of about 140 mOsm/kg to about 2,000 mOsm/kg.

74. The composition of claim 73 wherein said composition is formulated to have a pH of about 7 and an osmolality of about 750 mOsm/kg.

75. The composition of claim 73 wherein said composition has a pH of from about 4 to about 10 and has an osmolality of from about 140 mOsm/kg to about 2,000 mOsm/kg.

76. The composition of claim 73 which further comprises an energy source for white blood cells.

77. The composition of claim 76 wherein said energy source is selected from the group consisting of metabolic intermediates involved in energy production, monosaccharides, oligosaccharides, polysaccharides, metabolizable lipids, amino acids, oligopeptides and metabolizable proteins.

78. The composition of claim 73 wherein said energy source is selected from the group consisting of D-glucose, glucose-6-phosphate, fructose-6-phosphate, D-mannose, D-galactose, D-fructose, maltose, lactose, sucrose, glycogen, starch, fatty acids, neutral fats, pyruvic acid, lactic acid, citric acid and pharmaceutically acceptable salts thereof and mixtures thereof.

79. The composition of claim 78 wherein said energy source is D-glucose.

80. The composition of claim 73 wherein said source of cations provides the cations sodium, potassium, magnesium and calcium and the source of anions provides the anions chloride, sulfate, phosphate and bicarbonate.

81. The composition of claim 73 wherein said composition further comprises from about 0.5 to about 5.0 percent by weight acetic acid or a salt thereof.

82. The composition of claim 73 wherein said cellulose ether polymer is carboxymethylcellulose that has a molecular weight of from about 50,000 to about 1,000,000 daltons.

83. The composition of claim 73 wherein said chelating agent is selected from the group consisting of citric acid, EDTA, saccharic acid, NTA, HEEOTA, EDDHA, EGTA, DTPA, DCTA, N, N-bishydroxyethylglycine, HIMDA and salts thereof.

84. The composition of claim 83 wherein said chelator is citric acid or a salt thereof and said molar ratio is about 2.

85. A method for treating or preventing a condition in a mammal caused by the presence of a disease causing agent on a mucosal surface or a cutaneous surface wherein said disease causing agent can be diminished by the actions of the white blood cells of a mammal comprising contacting the mucosal surface or the cutaneous surface of said mammal in need of said treatment or prevention with an effective amount to treat or prevent said condition of a composition comprising:
(a) a source of cations to provide a cation selected from the group consisting of magnesium, calcium and mixtures thereof;
(b) a source of anions to provide an anion selected from the group consisting of phosphate, bicarbonate and mixtures thereof;
(c) a chelating agent capable of contributing to the stabilization of said composition;
(d) a cellulose ether polymer; and
(e) an energy source for white blood cells;
wherein the molar ratio of said chelating agent to the total numbers of moles of said calcium cations plus said magnesium cations is such that said composition results in no greater than about a 10% by weight decrease in the calcium plus magnesium concentration in said composition and the pH of said composition is from about 4 to about 10 and the osmolality of said composition is from about 140 mOsm/kg to about 2,000 mOsm/kg.

86. The method of claim 85 wherein said mucosal surface is the gingival mucosa and said condition is selected from the group consisting of gingivitis and dental plaque.

87. A method for healing a wound of a mucosal surface or cutaneous surface of a mammal comprising contacting the mucosal surface or the cutaneous surface of a mammal in need of said healing with a therapeutically effective amount of a composition comprising:
(a) a source of cations to provide a cation selected from the group consisting of magnesium, calcium and mixtures thereof;
(b) a source of anions to provide an anion selected from the group consisting of phosphate, bicarbonate and mixtures thereof;
(c) a chelating agent capable of contributing to the stabilization of said composition;
(d) a cellulose ether polymer; and
(e) an energy source for white blood cells;
wherein the molar ratio of said chelating agent to the total numbers of moles of said calcium cations plus said magnesium cations is such that said composition results in no greater than about a 10% by weight decrease in the calcium plus magnesium concentration in said composition after four weeks of storage at 42° C. and the pH of said composition is from about 4 to about 10 and the osmolality of said composition is from about 140 mOsm/kg to about 2,000 mOsm/kg.

88. A method for healing a wound of a mucosal surface or cutaneous surface of a mammal comprising contacting the mucosal surface or the cutaneous surface of a mammal in need of said healing with a therapeutically effective amount of a composition comprising:

(a) an energy source for white blood cells;

(b) a source of cations to provide a cation selected from the group consisting of sodium, potassium, magnesium, calcium and mixtures thereof;

(c) a source of anions to provide an anion selected from the group consisting of chloride, sulfate, phosphate, bicarbonate and mixtures thereof; and (d) acetic acid or a salt thereof;

wherein the pH of said composition is from about 4 to about 10 and the osmolality of said composition is from about 140 mOsm/kg to about 2,000 mOsm/kg.

89. A method for treating or preventing in a mammal a condition selected from the group consisting of oral, viral infections, oral fungal infections, oral radiation mucositis, the effects of radiation or antidepressant induced salivary dysfunction and the effects on oral soft tissues resulting from Xerostomia, which comprises contacting the oral mucosa or gingival mucosa of a mammal in need of said treatment or prevention with an effective amount to treat or prevent said condition of a composition comprising:

(a) an energy source for white blood cells;

(b) a source of cations to provide a cation selected from the group consisting of sodium, potassium, magnesium, calcium and mixtures thereof; and (c) a source of anions to provide an anion selected from the group consisting of chloride, sulfate, phosphate, bicarbonate and mixtures thereof;

wherein the pH of said composition is from about 4 to about 10 and the osmolality of said composition is from about 140 mOsm/kg to about 2,000 mOsm/kg.

90. The method of claim 89 wherein said fungal infection is oral Candidiasis.

91. The method of claim 89 wherein said viral infection is selected from the group consisting of herpes simplex virus infections, varicella virus infections and varicella zoster virus infections.

92. The method of claim 1 wherein said osmolality is between about 675 mOsm/Kg and 1460 mOsm/Kg.

93. The method of claim 41 wherein said osmolality is between about 675 mOsm/Kg and 1460 mOsm/Kg.

94. The composition of claim 73 wherein said osmolality is between about 675 mOsm/Kg and 1460 mOsm/Kg.

95. The method of claim 85 wherein said osmolality is between about 675 mOsm/Kg and 1460 mOsm/Kg.

96. The method of claim 87 wherein said osmolality is between about 675 mOsm/Kg and 1460 mOsm/Kg.

97. The method of claim 88 wherein said osmolality is between about 675 mOsm/Kg and 1460 mOsm/Kg.

98. The method of claim 89 wherein said osmolality is between about 675 mOsm/Kg and 1460 mOsm/Kg.

* * * * *